(12) United States Patent
Jensenius et al.

(10) Patent No.: US 6,969,601 B2
(45) Date of Patent: Nov. 29, 2005

(54) MASP-2, A COMPLEMENT-FIXING ENZYME, AND USES FOR IT

(76) Inventors: Jens Chr. Jensenius, Finsens Alle 28, Odense M, DK 5230 (DK); Steffen Thiel, Villadseusvei 3, Risskov DK 8240 (DK)

(*) Notice: Subject to any disclaimer, the term of this patent is extended or adjusted under 35 U.S.C. 154(b) by 399 days.

(21) Appl. No.: 09/874,198

(22) Filed: Jun. 4, 2001

(65) Prior Publication Data

US 2002/0082208 A1 Jun. 27, 2002

Related U.S. Application Data

(62) Division of application No. 09/054,218, filed on Apr. 2, 1998, now abandoned.
(60) Provisional application No. 60/042,678, filed on Apr. 3, 1997.

(51) Int. Cl.[7] .................... C12N 9/64; C07K 7/00; A61K 38/48
(52) U.S. Cl. ................ 435/226; 530/300; 514/2
(58) Field of Search .................. 435/226, 69.1, 435/252.3, 320.1; 530/300, 324, 417, 350; 514/2; 424/94.64; 536/23.2

(56) References Cited

U.S. PATENT DOCUMENTS

| | | | | |
|---|---|---|---|---|
| 5,270,199 A | | 12/1993 | Ezekowitz | 435/372.1 |
| 6,235,494 B1 | * | 5/2001 | Hugli | 435/24 |
| 6,297,024 B1 | * | 10/2001 | Hugli et al. | 435/23 |

OTHER PUBLICATIONS

Rasmussen, H.H., et al., 1996, "Towards a comprehensive database of proteins from the urine of patients with bladder cancer", Journal of Urology, vol. 155, pp. 2113–2119.*

Thiel, S., et al., 1997, "A second serine protease associated with mannan–binding lectin that activates complement", Nature, vol. 386, pp. 506–510.*

Stover, C. M., et al., 1999, "Two constituents of the initiation complex of the mannan–binding lectin activation pathway of complement are encoded by a single structural gene", Journal of Immunology, vol. 162, pp. 3481–3490.*

Seffernick et al., 2001, "Melamine Deaminase and Atrazine Chlorohydrolase: 98 Percent Identical but Functionally Different", Journal of Biochemistry, vol. 183, pp. 2405–2410.*

Garred, Peter, et al., "Increased frequency of homozygosity of abnormal mannan–binding–protein alleles in patients with suspected immunodeficiency", The Lancet, vol. 346, No. 8980, pp. 941–943, Oct. 1995.

Ikeda, Ken, et al., "Serum Lectin with Known Structure Activates Complement through the Classical Pathway", The Journal of Biological Chemistry, vol. 262, No. 16, pp. 7451–7454, Jun. 1987.

Ji, Yue–Hua, et al., "Activation of the C4 and C2 Components of Complement by a Proteinase in Serum Bactericidal Factor, Ra Reactive Factor", The Journal of Immunology, vol. 150, No. 2, pp. 571–576, Jan. 1993.

Matsushita, Misao, et al., Activation of the Classical Complement Pathway by Mannose–binding Protein in Assoc. with a Novel Cls–like Serine Protease, J. Exp. Med., vol. 176, pp. 1497–1502, Dec. 1992.

Nielsen, S.L., et al., "The level of the serum opsonin, mannan–binding protein in HIV–1 antibody–positive patients", Clinical and Experimental Immunology, vol. 100, No. 2, pp. 219–222, May 1995.

(Continued)

Primary Examiner—Ponnathaputa Achutamurthy
Assistant Examiner—William W. Moore
(74) Attorney, Agent, or Firm—Iver P. Cooper

(57) ABSTRACT

The invention relates to the discovery and characterization of mannan binding lectin-associated serine protease-2 (MASP-2), a new serine protease that acts in the MBLectin complement fixation pathway.

20 Claims, 6 Drawing Sheets

OTHER PUBLICATIONS

Sato, Tetsuo, et al., "Molecular characterization of a novel serine protease involved in activation of the Complement system by mannose–binding protein", *Int'l Immunology*, vol. 6, No. 4, pp. 665–669, Jan. 1994.

Sumiya, Michiko, et al., "Molecular basis of opsonic defect in immunodeficient children", *The Lancet*, vol. 337, pp. 1569–1570, Jun. 1991.

Summerfield, J.A. et al., "Mannose binding protein gene mutations associated with the unusual and severe infections in adults", The Lancet, vol. 345, No. 8954, pp. 886–889, Apr. 1995.

Thiel, Steffen, et al., "A second serine protease associated with mannan–binding lectin that activates complement", *Nature*, pp. 1–10, 1997.

Turner, Malcolm W., "Mannose–binding lectin: the pluripotent molecule of the innate immune system", *Immunology Today*, vol. 17, No. 11, pp. 532–540, Nov. 1996.

Kawasaki, T. et al., "Isolation and Characterization of a Mannan–Binding Protein From Rabbit Liver", *Biochem. Biophys. Res. Commun.*, 81:1018–1024 (1978).

Kawasaki, N. et al., "A Serum Lectin (Mannan–Binding Protein) Has Complement–Dependent Bactericidal Activity", *J. Biochem*, 106:483–489 (1989).

Kuhlman, Marcella et al., "The Human Mannose–Binding Protein Functions as an Opsonin", *J. Exp. Med.*, 169:1733–1745 (1989).

Lipscome, R.J. et al., "High frequencies in African non–African populations of independent mutations in the mannose–binding protein gene", *Hum. Mol. Genet.*, 1:709–715 (1992).

Madsen, Hans O. et al., "A new frequent allele is the missing link in the structural polymorphism of the human mannan-binding protein", *Immunogenetics*, 40:37–44 (1994).

Super, M. et al., "Association of Low Levels of Mannan–Binding Protein with a Common Defect of Opsonisation", *Lancet*, 11:1236–1239 (1989).

Garred, P. et al., "Susceptibility to HIV infection and progression of AIDS in relation to variant alleles of mannose–binding lectin", *Lancet*, 349:236–240 (1997).

Malhotra, Rajneesh et al., "Glycosylation changes of IgC associated with rheumatoid arthritis can activate complement via the mannose binding protein", *Nature Med.*, 1:237–243 (1995).

Davies, Eric J., "Mannose–binding Protein Gene Polymorphism in Systemic Lupus Erythematosus", *Arthritis Rheum.*, 38:110–114 (1995).

Jensenius, J.C. et al., "Mannan–binding lectin (MBL): From investigation on fish and chickens to substitutions therapy in an infant with severe infections", *Immunology*, 86:Suppl. 1, 100 abstract (1995).

Garred, P. et al., "Diallelic polymorphism may explain variations of the blood concentration of mannan–binding protein in eskimos, but not in black africans", *Eur. J. Immuno.*, 19:403–412 (1992).

Thiel, S. et al., Identification of a new mannan–binding protein associated serine protease (MASP–2), *Immunology*, 86:Suppl. 1, 101 (1995).

Baatrup, G. et al., "Demonstration in Human Plasma of a Lectin Activity Analogous to that of Bovine Conglutinin", *Scand. J. Immunol.*, 26:355–361 (1987).

Jensenius, J.C. et al., "EGGS: Conveniently Packaged Antibodies. Methods for purification of yolk lgG", *Immunol. Methods*, 46:63–66 (1981).

Endo, Y. et al., "Exon structure of the gene encoding the human mannose–binding protein–associated serine protease light chain: comparison with complement Clr and Cls genes", *Int. Immunol.*, 9:1355–1358 (1996).

Tan, Suet et al., "Improvements on the purification of mannan–binding lectin and demonstration of its $CA^{2}+$ independent association with a Cls–like serine protease", *Biochem. J.*, 319:329–332 (1996).

Barton, Geoffrey J., "Protein Multiple Sequence Alignment and Flexible Pattern Matching", *Methods Enzymol.*, 183:403–428 (1990).

Takada, Fumio et al., "A new member of the Cls family of complement proteins found in a bactericidal factor, Ra–reactive factor, in human serum", *Biochem.Biophys. Res. Comm.*, 196:1003–1009 (1993).

Journet, Agnes et al., "Cloning and sequencing of full-length cDNA encoding the precursor of human complement component Clr", *Biochem J.*, 240:783–787 (1986).

Leytus, Steven P. et al., "Nucleotide Sequence of the cDNA Coding for Human Complement Clr", *Biochemistry*, 25:4855–4863 (1986).

MacKinnon, Charlotte M. et al., "Molecular cloning of cDNA for human complement component Cls. The complete amino acid sequence", *Eur. J. Biochem.*, 169:547–553 (1987).

Tosi, Mario, "Complete cDNA Sequence of Human Complement Cls and Close Physical Linkage of the Homologous Genes Cls and Clr", *Biochemistry*, 26:8516–8524 (1987).

* cited by examiner

Figure 2

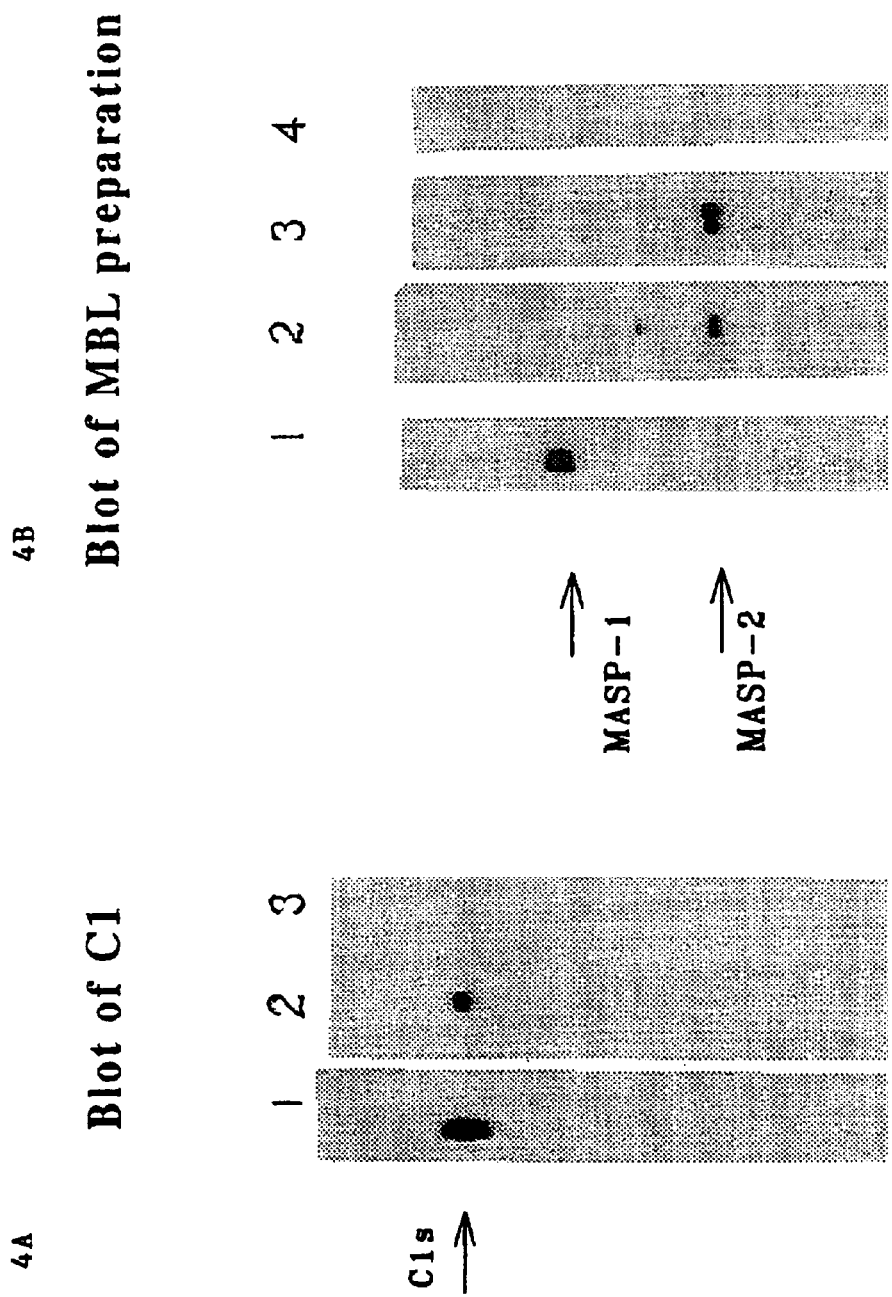

Figure 6

MASP-2, A COMPLEMENT-FIXING ENZYME, AND USES FOR IT

CROSS REFERENCE TO RELATED APPLICATION

This application is a divisional (and claims the benefit of under 35 USC 120) of U.S. application Ser. No. 09/054,218, filed Apr. 2, 1998, now abandoned, which claims priority from U.S. Provisional Application Ser. No. 60/042,678, filed Apr. 3, 1997. The disclosure of the prior application is considered part of (and is incorporated by reference in) the disclosure of this application.

FIELD OF THE INVENTION

The invention is in the general field of innate pathways for complement fixation involving mannan-binding lectin (MBL), also termed mannan binding protein.

BACKGROUND OF THE INVENTION

The complement system comprises a complex array of enzymes and non-enzymatic proteins of importance to the function of the innate as well as the adaptive immune defense[1]. Until recently two modes of activation were known, the classical pathway initiated by antibody-antigen complexes and the alternative pathway initiated by certain structures on microbial surfaces. A third, novel antibody-independent pathway of complement activation has been described[2]. This pathway is initiated when mannan-binding lectin (MBL, first described as mannan-binding protein, MBP, see Ezekowitz, U.S. Pat. No. 5,270,199) binds to carbohydrates.

MBL is structurally related to the C1q subcomponent of component C1 of complement, and it appears that MBL activates the complement system via an associated serine protease termed MASP[4] or p100[5], which is similar to the C1r and C1s components of the classical pathway. The new complement activation pathway is called the MBLectin pathway. According to the mechanism postulated for this pathway, MBL binds to specific carbohydrate structures found on the surface of a range of microorganisms including bacteria, yeast, parasitic protozoa and viruses[6], and its antimicrobial activity results from activation of the terminal, lytic complement pathway components[7] or promoting phagocytosis[8].

Reportedly, the level of MBL in plasma may be genetically determined[9,10,11]. MBL deficiency is associated with susceptibility to frequent infections with a variety of microorganisms in childhood[12,13], and, possibly, in adults[13,14]. Recent information associates MBL deficiency with HIV infection and with more rapid death following development of AIDS[15,16]. MBL binds to the a galactosyl form of IgG (G0), which is found at elevated concentrations in rheumatoid arthritis patients, and then activates complement[17]. MBL deficiency is also associated with a predisposition to recurrent spontaneous abortions[18], and also to development of systemic lupus erythrematosus[19].

In the first clinical reconstitution trial, an infant MBL-deficient girl suffering from recurrent infections was apparently cured by injections with purified MBL[20]. For a recent review on MBL, see ref. 6.

Relatively high frequencies of MBL mutations associated with MBL-deficiency have been reported in all populations studied. This observation has led to the hypothesis that MBL may, in certain cases, render the individual more susceptible to certain intracellular infectious agents exploiting MBL to gain access to the target tissues[21]. Since MBL is a very powerful activator of the complement system, it may also be that inexpedient activation through microbial carbohydrates or endotoxins can lead to damaging inflammatory responses[10]. Thus, the overall survival of a population may benefit from the wide individual range of MBL concentrations.

MASP-1 (MBP-associated serine protease, MASP) is a serine protease similar in structure to C1r and C1s of the complement pathway although it has a histidine loop structure of the type found in trypsin and trypsin-like serine proteases. MASP-1 has been found to be involved in complement activation by MBL. A cDNA clone encoding MASP-1 has been reported that encodes a putative leader peptide of 19 amino acids followed by 680 amino acid residues predicted to form the mature peptide.

An abstract reports the existence of a second MASP, termed MASP-2.[22]

SUMMARY OF THE INVENTION

The invention relates to the isolation and characterization of a mannan-binding lectin (MBL) associated serine protease (MASP-2). MASP-2 shows some homology with the previously reported MASP (MASP-1) and the two C1q-associated serine proteases, C1r and C1s. MBL alone does not provide a functional MBLectin pathway of complement activation.

We have cloned and sequenced the cDNA encoding MASP-2. In addition, we have produced anti-MASP-2 antibody and constructed an assay for the estimation of MASP-2 in body fluids or tissue extracts. Furthermore, we have constructed quantitative assays for the determination of MASP-2 activity in serum or plasma, either when present as part of the MBL/MASP complex or as free MASP not associated with MBL.

Thus, one aspect of the invention features substantially pure mannin-binding lectin associated serine protease-2 (MASP-2) polypeptides and nucleic acids encoding such polypeptides. Preferably, the MASP-2 polypeptide retains one or more MASP-2 functions, such as being capable of associating with mannan-binding lectin (MBL), serine protease activity, or the MASP-2 activity in an in vitro assay for MBLectin complement pathway function, e.g., in one of the assay systems described below. Some MASP-2 polypeptides according to the invention, e.g., those used in binding assays, may be conjugated to a label so as to permit detection and/or quantification of their presence in the assay. Suitable labels include enzymes which generate a signal (e.g., visible absorption), fluorophores, radionuclides, etc. Other MASP-2 polypeptides are capable of competitively inhibiting one of the MASP-2 activities described above, and thereby are useful in evaluating MASP-2 function. Other MASP-2 polypeptides are useful antigens or haptens for producing antibodies as described below. Compounds which competitively inhibit a MASP-2 activity are also featured. Preferably, such compounds act by inhibiting the serine protease activity of MASP-2 or of a fragment of MASP-2. Such compounds may include fragments of MBL or of MASP-2 which competitively inhibit the MBL-MASP-2 interactions critical to complement activation by the MBLectin pathway, as well as compounds, e.g., peptide fragments, which inhibit the catalytic cleavage of complement factors C4 and C2 by MASP-2.

Specific polypeptides according to this aspect of the invention include: a) a polypeptide with a molecular mass of 20K and containing the sequence identified as SEQ ID NO:1

[T P L G P K W P E P V F G R L A S P G F P G E Y A N D Q E R R W T L T A P P G Y R]; b) a polypeptide with a molecular mass of 52K and containing the sequence identified as SEQ ID NO:1; c) a polypeptide having the complete amino acid sequence of FIG. 6 (SEQ ID NO:2).

Another aspect of the invention includes an isolated nucleic acid molecule comprising a nucleotide sequence encoding a polypeptide having sequence that is at least 85% identical to the sequence of SEQ ID NO:2.

The invention also features isolated nucleic acid sequences encoding the above mannan-binding lectin associated serine protease-2 (MASP-2) polypeptides. Such nucleic acid sequences may be included in nucleic acid vectors (e.g., expression vectors including those with regulatory nucleic acid elements permitting expression of recombinant nucleic acid in an expression system).

The invention also features antibodies that selectively bind to MASP-2. Such antibodies may be made by any of the well known techniques including polyclonal and monoclonal antibody techniques. The antibody may be coupled to a compound comprising a detectable marker, so that it can be used, e.g. in an assay to detect MASP-2.

The polypeptides or antibodies may be formulated into pharmaceutical compositions and administered as therapeutics as described below.

The invention also features methods for detecting mannan-binding lectin associated serine protease-2 (MASP-2). The method comprises; obtaining a biological sample, contacting the biological sample with a MASP-2 polypeptide specific binding partner, and detecting the bound complexes, if any, as an indication of the presence of MASP-2 in the biological sample. The binding partner used in the assay may be an antibody, or the assay for MASP-2 may test for complement fixing activity. These assays for MASP-2 may also be used for quantitative assays of MASP-2 or MASP-2 activity in biological samples. One of the binding parners may be specific for MBK thus allowing for the detection of MBL/MASP-2 complexes.

Methods for detecting MASP-2 nucleic acid expression are included in the invention. These methods comprise detecting RNA having a sequence encoding a MASP-2 polypeptide by mixing the sample with a nucleic acid probe that specifically hybridizes under stringent conditions to a nucleic acid sequence encoding all or a fragment of MASP-2.

The invention also features methods for treating patients deficient in MASP-2 or MASP-2 activity. This is accomplished by administering to the patient MASP-2 polypeptide or nucleic acid encoding MASP-2. Because it is sometimes desirable to inhibit MASP-2 activity, the invention includes a method for inhibiting the activity of MASP-2 by administering to the patient a compound that inhibits expression or activity of MASP-2. Inhibition of MASP-2 activity may also be achieved by administering a MASP-2 anti-sense nucleic acid sequence.

The invention features an assay for polymorphisms in the nucleic acid sequence encoding MASP-2. A method of detecting the presence of MASP-2-encoding nucleic acid in a sample is claimed. As an example, the method may include mixing the sample with at least one nucleic acid probe capable of forming a complex with MASP-2-encoding nucleic acid under stringent conditions, and determining whether the probe is bound to sample nucleic acid. The invention thus includes nucleic acid probe capable of forming a complex with MASP-2-encoding nucleic acid under stringent conditions.

The invention features an assay for polymorphisms in the polypeptide sequence comprising MASP-2 or its precursor.

MASP-2 assays are useful for the determination of MASP-2 levels and MASP-2 activity in patients suffering from various diseases such as infections, inflammatory diseases and spontaneous recurrent abortion. MASP-2 is useful for the treatment of infections when MASP-2 function is suboptimal, and inhibition of MASP-2 activity is useful for regulation of inflammation and adverse effects caused by activity of the MBLectin pathway.

By "mannan-binding lectin associated serine protease-2" or "MASP-2" is meant the polypeptide or activity called "mannan-binding protein associated serine protease-2" or "mannose-binding protein associated serine protease" or any other polypeptide having substantial sequence identity with SEQ ID NO:2.

The terms "protein" and "polypeptide" are used herein to describe any chain of amino acids, regardless of length or post-translational modification (for example, glycosylation or phosphorylation). Thus, the term "MASP-2 polypeptide" includes full-length, naturally occurring MASP-2 protein, as well as recombinantly or synthetically produced polypeptide that corresponds to a full-length naturally occurring MASP-2 polypeptide, or to particular domains or portions of a naturally occurring protein. The term also encompassses mature MASP-2 which has an added amino-terminal methionine (which is useful for expression in prokaryotic cells).

The term "purified" as used herein refers to a nucleic acid or peptide that is substantially free of cellular material, viral material, or culture medium when produced by recombinant DNA techniques, or chemical precursors or other chemicals when chemically synthesized.

By "isolated nucleic acid molecule" is meant a nucleic acid molecule that is separated in any way from sequences in the naturally occurring genome of an organism. Thus, the term "isolated nucleic acid molecule" includes nucleic acid molecules which are not naturally occurring, e.g., nucleic acid molecules created by recombinant DNA techniques.

The term "nucleic acid molecule" encompasses both RNA and DNA, including cDNA, genomic DNA, and synthetic (e.g., chemically synthesized) DNA. Where single-stranded, the nucleic acid may be a sense strand or an antisense strand.

The invention also encompasses nucleic acid molecules that hybridize, preferably under stringent conditions, to a nucleic acid molecule encoding an MASP-2 polypeptide (e.g., a nucleic-acid molecule having the sequence encoding SEQ ID NO:2, e.g., the protein encoding portion of the cDNA sequence shown in FIG. 6—SEQ ID NO:3). In addition, the invention encompasses nucleic acid molecules that hybridize, preferably under stringent conditions, to a nucleic acid molecule having the sequence of the MASP-2 encoding cDNA contained in a clone. Preferably the hybridizing nucleic acid molecule consists of 400, more preferably 200 nucleotides.

Preferred hybridizing nucleic acid molecules encode an activity possessed by MASP-2, e.g., they bind MBL and have activity in the MBLectin complement pathway, and can act as serine proteases.

The invention also features substantially pure or isolated MASP-2 polypeptides, preferably those that correspond to various functional domains of MASP-2, or fragments thereof. The polypeptides of the invention encompass amino acid sequences that are substantially identical to the amino acid sequence shown in FIG. 6.

The polypeptides of the invention can also be chemically synthesized, synthesized by recombinant technology, or they can be purified from tissues in which they are naturally expressed, according to standard biochemical methods of purification.

Also included in the invention are "functional polypeptides" which possess one or more of the biological functions or activities of MASP-2. These functions or activities are described in detail in the specification. A functional polypeptide is also considered within the scope of the invention if it serves as an antigen for production of antibodies that specifically bind to MASP-2 or fragments (particularly determinant containing fragments) thereof.

The functional polypeptides may contain a primary amino acid sequence that has been modified from those disclosed herein. Preferably these modifications consist of conservative amino acid substitutions, as described herein. The polypeptides may be substituted in any manner designed to promote or delay their catabolism (increase their half-life).

Polypeptides or other compounds of interest are said to be "substantially pure" when they are distinct from any naturally occuring composition, and suitable for at least one of the uses proposed herein. While preparations that are only slightly altered with respect to naturally occuring substances may be somewhat useful, more typically, the preparations are at least 10% by weight (dry weight) the compound of interest. Preferably, the preparation is at least 60%, more preferably at least 75%, and most preferably at least 90%, by weight the compound of interest. Purity can be measured by any appropriate standard method, for example, by column chromatography, polyacrylamide gel electrophoresis, or HPLC analysis.

A polypeptide or nucleic acid molecule is "substantially identical" to a reference polypeptide or nucleic acid molecule if it has a sequence that is at least 85%, preferably at least 90%, and more preferably at least 95%, 98%, or 99% identical to the sequence of the reference polypeptide or nucleic acid molecule.

Where a particular polypeptide is said to have a specific percent identity to a reference polypeptide of a defined length, the percent identity is relative to the reference peptide. Thus, a peptide that is 50% identical to a reference polypeptide that is 100 amino acids long can be a 50 amino acid polypeptide that is completely identical to a 50 amino acid long portion of the reference polypeptide. It might also be a 100 amino acid long polypeptide which is 50% identical to the reference polypeptide over its entire length. Of course, many other polypeptides will meet the same criteria.

In the case of polypeptide sequences which are less than 100% identical to a reference sequence, the non-identical positions are preferably, but not necessarily, conservative substitutions for the reference sequence. Conservative substitutions typically include substitutions within the following groups: glycine and alanine; valine, isoleucine, and leucine; aspartic acid and glutamic acid; asparagine and glutamine; serine and threonine; lysine and arginine; and phenylalanine and tyrosine.

For polypeptides, the length of the reference polypeptide sequence will generally be at least 16 amino acids, preferably at least 20 amino acids, more preferably at least 25 amino acids, and most preferably 35 amino acids, 50 amino acids, or 100 amino acids. For nucleic acids, the length of the reference nucleic acid sequence will generally be at least 50 nucleotides, preferably at least 60 nucleotides, more preferably at least 75 nucleotides, and most preferably 100 nucleotides or 300 nucleotides.

Sequence identity can be measured using sequence analysis software (for example, the Sequence Analysis Software Package of the Genetics Computer Group, University of Wisconsin Biotechnology Center, 1710 University Avenue, Madison, Wis. 53705), with the default parameters as specified therein.

The nucleic acid molecules of the invention can be inserted into a vector, as described below, which will facilitate expression of the insert. The nucleic acid molecules and the polypeptides they encode can be used directly as diagnostic or therapeutic agents, or can be used (directly in the case of the polypeptide or indirectly in the case of a nucleic acid molecule) to generate antibodies that, in turn, are clinically useful as a therapeutic or diagnostic agent. Accordingly, vectors containing the nucleic acid of the invention, cells transfected with these vectors, the polypeptides expressed, and antibodies generated, against either the entire polypeptide or an antigenic fragment thereof, are among the preferred embodiments.

The invention also features antibodies, e.g., monoclonal, polyclonal, and engineered antibodies, which specifically bind MASP-2. By "specifically binds" is meant an antibody that recognizes and binds to a particular antigen, e.g., the MASP-2 polypeptide of the invention, but which does not substantially recognize or bind to other molecules in a sample, e.g., a biological sample, which includes MASP-2. References to constructs of antibody (or fragment thereof) coupled to a compound comprising a detectable marker includes constructs made by any technique, including chemical means or by recombinant techniques.

The invention also features antagonists and agonists of MASP-2 that can inhibit or enhance one or more of the functions or activities of MASP-2, respectively. Suitable antagonists can include small molecules (i.e., molecules with a molecular weight below about 500), large molecules (i.e., molecules with a molecular weight above about 500), antibodies that bind and "neutralize" MASP-2 (as described below), polypeptides which compete with a native form of MASP-2 for binding to a protein, e.g., MBL, and nucleic acid molecules that interfere with transcription of MASP-2 (for example, antisense nucleic acid molecules and ribozymes). Agonists of MASP-2 also include small and large molecules, and antibodies other than "neutralizing" antibodies.

The invention also features molecules which can increase or decrease the expression of MASP-2 (e.g., by influencing transcription or translation). Small molecules (i.e., molecules with a molecular weight below about 500), large molecules (i.e., molecules with a molecular weight above about 500), and nucleic acid molecules that can be used to inhibit the expression of MASP-2 (for example, antisense and ribozyme molecules) or to enhance their expression (for example, expression constructs that place nucleic acid sequences encoding MASP-2 under the control of a strong promoter system), and transgenic animals that express a MASP-2 transgene.

The invention encompasses methods for treating disorders associated with aberrant expression or activity of MASP-2. Thus, the invention includes methods for treating disorders associated with excessive expression or activity of MASP-2. Such methods entail administering a compound which decreases the expression or activity of MASP-2. The invention also includes methods for treating disorders associated with insufficient expression of MASP-2. These methods entail administering a compound which increases the expression or activity of MASP-2.

By "competitively inhibiting" serine protease activity is meant that, for example, the action of an altered MBL or fragment thereof that can bind to a MASP-2 peptide, reversibly or irreversibly without activating serine protease activity. Conversely, a fragment of MASP-2, e.g., a polypeptide encompassing the N-terminal part of MASP-2, may competitively inhibit the binding of the intact MASP-2 and thus effectively inhibit the activation of MASP-2.

The invention also features methods for detecting a MASP-2 polypeptide. Such methods include: obtaining a biological sample; contacting the sample with an antibody that specifically binds MASP-2 under conditions which permit specific binding; and detecting any antibody-MASP-2 complexes formed.

In addition, the present invention encompasses methods and compositions for the diagnostic evaluation, typing, and prognosis of disorders associated with inappropriate expression or activity of MASP-2. For example, the nucleic acid molecules of the invention can be used as diagnostic hybridization probes to detect, for example, inappropriate expression of MASP-2 or mutations in the MASP-2 gene. Such methods may be used to classify cells by the level of MASP-2 expression.

Alternatively, the nucleic acid molecules can be used as primers for diagnostic PCR analysis for the identification of gene mutations, allelic variations and regulatory defects in the MASP-2 gene. The present invention further provides for diagnostic kits for the practice of such methods.

The invention features methods of identifying compounds that modulate the expression or activity of MASP-2 by assessing the expression or activity of MASP-2 in the presence and absence of a selected compound. A difference in the level of expression or activity of MASP-2 in the presence and absence of the selected compound indicates that the selected compound is capable of modulating expression or activity or MASP-2. Expression can be assessed either at the level of gene expression (e.g., by measuring mRNA) or protein expression by techniques that are well known to skilled artisans. The activity of MASP-2 can be assessed functionally, i.e., by assaying the ability of the compound to activate complement.

The preferred methods and materials are described below in examples which are meant to illustrate, not limit, the invention. Skilled artisans will recognize methods and materials that are similar or equivalent to those described herein, and that can be used in the practice or testing of the present invention.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, the preferred methods and materials are described herein. All publications, patent applications, patents, and other references mentioned herein are incorporated by reference in their entirety. In the case of conflict, the present specification, including definitions, will control. In addition, the materials, methods, and examples are illustrative only and are not intended to be limiting.

Other features and advantages of the invention will be apparent from the detailed description, and from the claims.

BRIEF DESCRIPTION OF THE DRAWINGS

FIG. 2 shows the sequence alignments of the amino acid sequences of MASP-2 (clone phl-4) (SEQ ID NO:2), MASP-1[17,22] (SEQ ID NO:6 ), C1r[23,24] (SEQ ID NO:7) and C1s[25,26] (SEQ ID NO:8).

FIGS. 4a–4b are representations of Western blots demonstrating the activation of C4 by C1s and MASP-2.

FIG. 6 shows the cDNA sequence (SEQ ID NO:3) and deduced amino acid (SEQ ID NO:2) sequence of MASP-2.

DESCRIPTION OF THE PREFERRED EMBODIMENTS

MASP-2 Nucleic Acid Molecules

Figure 1B:
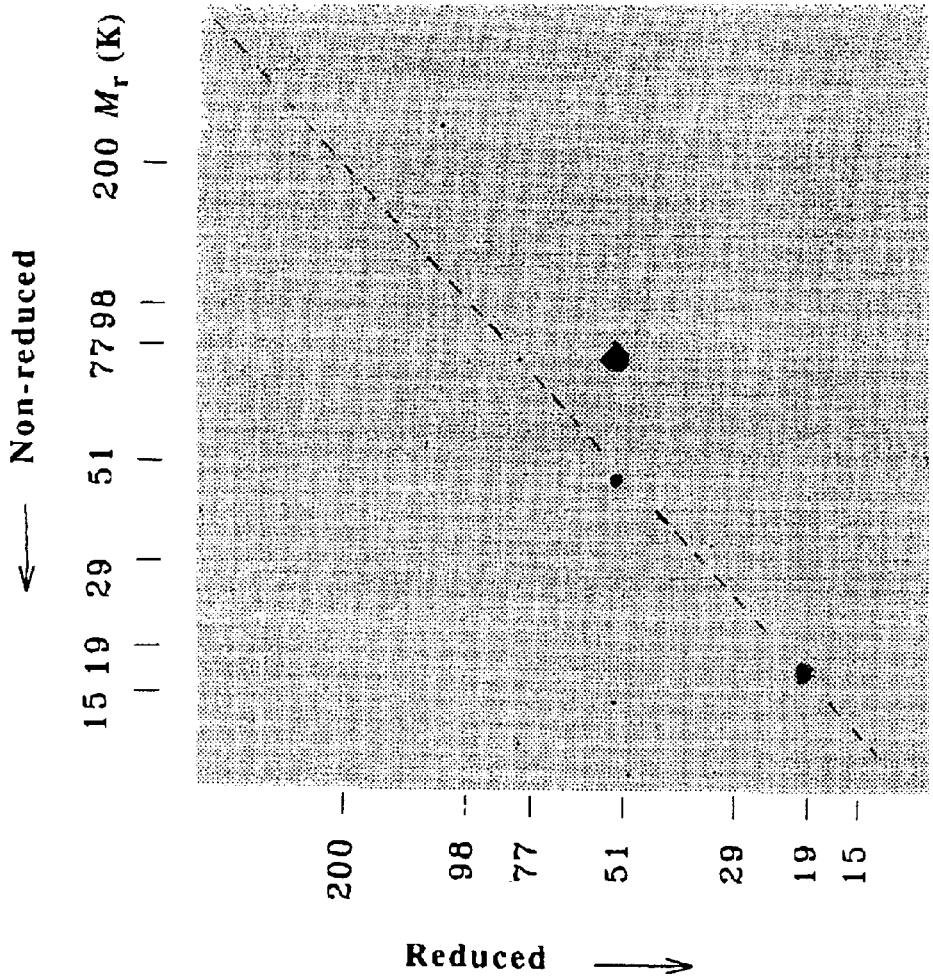
FIGS. 1a–1b depict a Western blot of human plasma proteins purified by sugar affinity chromatography.

The MASP-2 nucleic acid molecules of the invention can be cDNA, genomic DNA, synthetic DNA, or RNA, and can be double-stranded or single-stranded (i.e., either a sense or an antisense strand). Fragments of these molecules are also considered within the scope of the invention, and can be produced, for example, by the polymerase chain reaction (PCR) or generated by treatment with one or more restriction endonucleases. A ribonucleic acid (RNA) molecule can be produced by in vitro transcription. Preferably, the nucleic acid molecules encode polypeptides that, regardless of length, are soluble under normal physiological conditions.

The nucleic acid molecules of the invention can contain naturally occurring sequences, or sequences that differ from those that occur naturally, but, due to the degeneracy of the genetic code, encode the same polypeptide (for example, the polypeptide of SEQ ID NO:2). In addition, these nucleic acid molecules are not limited to sequences that only encode polypeptides, and thus, can include some or all of the non-coding sequences that lie upstream or downstream from a coding sequence.

The nucleic acid molecules of the invention can be synthesized (for example, by phosphoramidite-based synthesis) or obtained from a biological cell, such as the cell of a mammal. Thus, the nucleic acids can be those of a human, mouse, rat, guinea pig, cow, sheep, horse, pig, rabbit, monkey, dog, or cat. Combinations or modifications of the nucleotides within these types of nucleic acids are also encompassed.

In addition, the isolated nucleic acid molecules of A the invention encompass fragments that are not found as such in the natural state. Thus, the invention encompasses recombinant molecules, such as those in which a nucleic acid molecule (for example, an isolated nucleic acid molecule encoding MASP-2) is incorporated into a vector (for example, a plasmid or viral vector) or into the genome of a heterologous cell (or the genome of a homologous cell, at a position other than the natural chromosomal location). Recombinant nucleic acid molecules and uses therefore are discussed further below.

In the event the nucleic acid molecules of the invention encode or act as antisense molecules, they can be used for example, to regulate translation of MASP-2. Techniques associated with detection or regulation of nucleic acid expression are well known to skilled artisans and can be used to diagnose and/or treat disorders associated with MASP-2 activity. These nucleic acid molecules are discussed further below in the context of their clinical utility.

The invention also encompasses nucleic acid molecules that hybridize under stringent conditions to a nucleic acid molecule encoding a MASP-2 polypeptide. The cDNA sequence described herein (SEQ ID NO:3) can be used to identify these nucleic acids, which include, for example, nucleic acids that encode homologous polypeptides in other species, and splice variants of the MASP-2 gene in humans or other mammals. Accordingly, the invention features methods of detecting and isolating these nucleic acid molecules. Using these methods, a sample (for example, a nucleic acid library, such as a cDNA or genomic library) is contacted (or "screened") with a MASP-2-specific probe (for example, a fragment of SEQ ID NO:3 that is at least 12 nucleotides long). The probe will selectively hybridize to nucleic acids encoding related polypeptides (or to complementary sequences thereof). Because the polypeptide encoded by MASP-2 is related to other serine proteases, the term "selectively hybridize" is used to refer to an event in which a probe binds to nucleic acids encoding MASP-2 (or to complementary sequences thereof) to a detectably greater extent than to nucleic acids encoding other serine proteases (or to complementary sequences thereof). The probe, which can contain at least 12 (for example, 15, 25, 50, 100, or 200 nucleotides) can be produced using any of several standard methods (see, for example, Ausubel et al.,"Current Protocols in Molecular Biology, Vol. I," Green Publishing Associates, Inc., and John Wiley & Sons, Inc., NY, 1989). For example, the probe can be generated using PCR amplification methods in which oligonucleotide primers are used to amplify a MASP-2-specific nucleic acid sequence (for example, a nucleic acid encoding the N-terminus of mature MASP-2) that can be used as a probe to screen a nucleic acid library, as described in Example 4 below, and thereby detect nucleic acid molecules (within the library) that hybridize to the probe.

One single-stranded nucleic acid is said to hybridize to another if a duplex forms between them. This occurs when one nucleic acid contains a sequence that is the reverse and complement of the other (this same arrangement gives rise to the natural interaction between the sense and antisense strands of DNA in the genome and underlies the configuration of the "double helix"). Complete complementarity between the hybridizing regions is not required in order for a duplex to form; it is only necessary that the number of paired bases is sufficient to maintain the duplex under the hybridization conditions used.

Typically, hybridization conditions are of low to moderate stringency. These conditions favor specific interactions between completely complementary sequences, but allow some non-specific interaction between less than perfectly matched sequences to occur as well. After hybridization, the nucleic acids can be "washed" under moderate or high conditions of stringency to dissociate duplexes that are bound together by some non-specific interaction (the nucleic acids that form these duplexes are thus not completely complementary).

As is known in the art, the optimal conditions for washing are determined empirically, often by gradually increasing the stringency. The parameters that can be changed to affect stringency include, primarily, temperature and salt concentration. In general, the lower the salt concentration and the higher the temperature, the higher the stringency. Washing can be initiated at a low temperature (for example, room temperature) using a solution containing a salt concentration that is equivalent to or lower than that of the hybridization solution. Subsequent washing can be carried out using progressively warmer solutions having the same salt concentration. As alternatives, the salt concentration can be lowered and the temperature maintained in the washing step, or the salt concentration can be lowered and the temperature increased. Additional parameters can also be altered. For example, use of a destabilizing agent, such as formamide, alters the stringency conditions.

In reactions where nucleic acids are hybridized, the conditions used to achieve a given level of stringency will vary. There is not one set of conditions, for example, that will allow duplexes to form between all nucleic acids that are 85% identical to one another; hybridization also depends on unique features of each nucleic acid. The length of the sequence, the composition of the sequence (for example, the content of purine-like nucleotides versus the content of pyrimidine-like nucleotides) and the type of nucleic acid (for example, DNA or RNA) affect hybridization. An additional consideration is whether one of the nucleic acids is immobilized (for example, on a filter).

An example of a progression from lower to higher stringency conditions is the following, where the salt content is given as the relative abundance of SSC (a salt solution containing sodium chloride and sodium citrate; 2×SSC is 10-fold more concentrated than 0.2×SSC). Nucleic acids are hybridized at 42° C. in 2×SSC/0.1% SDS (sodium dodecylsulfate; a detergent) and then washed in 0.2×SSC/0.1% SDS at room temperature (for conditions of low stringency); 0.2×SSC/0.1% SDS at 42° C. (for conditions of moderate stringency); and 0.1×SSC at 68° C. (for conditions of high stringency). Washing can be carried out using only one of the conditions given, or each of the conditions can be used (for example, washing for 10–15 minutes each in the order listed above). Any or all of the washes can be repeated. As mentioned above, optimal conditions will vary and can be determined empirically.

A second set of conditions that are considered "stringent conditions" are those in which hybridization is carried out at 50° C. in Church buffer (7% SDS, 0.5% $NaHPO_4$, 1 M EDTA, 1% bovine serum albumin) and washing is carried out at 50° C. in 2×SSC.

Once detected, the nucleic acid molecules can be isolated by any of a number of standard techniques (see, for example, Sambrook et al., "Molecular Cloning, A Laboratory Manual," 2nd Ed. Cold Spring Harbor Laboratory Press, Cold Spring Harbor, N.Y., 1989).

The invention also encompasses: (a) expression vectors that contain any of the foregoing MASP-2-related coding sequences and/or their complements (that is, "antisense" sequence); (b) expression vectors that contain any of the foregoing MASP-2-related coding sequences operatively associated with a regulatory element (examples of which are given below) that directs the expression of the coding sequences; (c) expression vectors containing, in addition to sequences encoding a MASP-2 polypeptide, nucleic acid sequences that are unrelated to nucleic acid sequences encoding MASP-2, such as molecules encoding a reporter or marker; and (d) genetically engineered host cells that contain any of the foregoing expression vectors and thereby express the nucleic acid molecules of the invention in the host cell.

Recombinant nucleic acid molecule can contain a sequence encoding a soluble MASP-2, mature MASP-2, MASP-2 having a signal sequence, or functional domains of MASP-2 such as the serine protease domain, EGF domain, or the MBL-binding domain. The full length MASP-2 polypeptide, a domain of MASP-2, or a fragment thereof may be fused to additional polypeptides, as described below. Similarly, the nucleic acid molecules of the invention can encode the mature form of MASP-2 or a form that encodes a polypeptide which facilitates secretion. In the latter instance, the polypeptide is typically referred to as a proprotein, which can be converted into an active form by removal of the signal sequence, for example, within the host cell. Proproteins can be converted into the active form of the protein by removal of the inactivating sequence.

The regulatory elements referred to above include, but are not limited to, inducible and non-inducible promoters, enhancers, operators and other elements, which are known to those skilled in the art, and which drive or otherwise regulate gene expression. Such regulatory elements include but are not limited to the cytomegalovirus hCMV immediate early gene, the early or late promoters of SV40 adenovirus, the lac system, the trp system, the TAC system, the TRC system, the major operator and promoter regions of phage A, the control regions of fd coat protein, the promoter for 3-phosphoglycerate kinase, the promoters of acid phosphatase, and the promoters of the yeast α-mating factors.

Similarly, the nucleic acid can form part of a hybrid gene encoding additional polypeptide sequences, for example, sequences that function as a marker or reporter. Examples of marker or reporter genes include β-lactamase, chloramphenicol acetyltransferase (CAT), adenosine deaminase (ADA), aminoglycoside phosphotransferase (neo$^r$, G418$^r$), dihydrofolate reductase (DHFR), hygromycin-B-phospohotransferase (HPH), thymidine kinase (TK), lacZ (encoding β-galactosidase) green fluorescent protein (GFP), and xanthine guanine phosphoribosyltransferase (XGPRT). As with many of the standard procedures associated with the practice of the invention, skilled artisans will be aware of additional useful reagents, for example, of additional sequences that can serve the function of a marker or reporter. Generally, the hybrid polypeptide will include a first portion and a second portion; the first portion being a MASP-2 polypeptide and the second portion being, for example, the reporter described above or an immunoglobulin constant region.

The expression systems that may be used for purposes of the invention include, but are not limited to, microorganisms such as bacteria (for example, *E. coli* and *B. subtilis*) transformed with recombinant bacteriophage DNA, plasmid DNA, or cosmid DNA expression vectors containing the nucleic acid molecules of the invention; yeast (for example, *Saccharomyces* and *Pichia*) transformed with recombinant yeast expression vectors containing the nucleic acid molecules of the invention (preferably containing the nucleic acid sequence of MASP-2 (SEQ ID NO:3)); insect cell systems infected with recombinant virus expression vectors (for example, baculovirus) containing the nucleic acid molecules of the invention; plant cell systems infected with recombinant virus expression vectors (for example, cauliflower mosaic virus (CaMV) and tobacco mosaic virus (TMV)) or transformed with recombinant plasmid expression vectors (for example, Ti plasmid) containing MASP-2 nucleotide sequences; or mammalian cell systems (for example, COS, CHO, BHK, 293, VERO, HeLa, MDCK, WI38, and NIH 3T3 cells) harboring recombinant expression constructs containing promoters derived from the genome of mammalian cells (for example, the metallothionein promoter) or from mammalian viruses (for example, the adenovirus late promoter and the vaccinia virus 7.5K promoter).

In bacterial systems, a number of expression vectors may be advantageously selected depending upon the use intended for the gene product being expressed. For example, when a large quantity of such a protein is to be produced, for the generation of pharmaceutical compositions containing MASP-2 polypeptides or for raising antibodies to those polypeptides, vectors that are capable of directing the expression of high levels of fusion protein products that are readily purified may be desirable. Such vectors include, but are not limited to, the *E. coli* expression vector pUR278 (Ruther et al., *EMBO J.* 2:1791, 1983), in which the coding sequence of the insert may be ligated individually into the vector in frame with the lacZ coding region so that a fusion protein is produced; pIN vectors (Inouye and Inouye, *Nucleic Acids Res.* 13:3101–3109, 1985; Van Heeke and Schuster, *J. Biol. Chem.* 264:5503–5509, 1989); and the like, pGEX vectors may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. The pGEX vectors are designed to include thrombin or factor Xa protease cleavage sites so that the cloned target gene product can be released from the GST moiety.

In an insect system, *Autographa californica* nuclear polyhidrosis virus (AcNPV) can be used as a vector to express foreign genes. The virus grows in *Spodoptera frugiperda* cells. The coding sequence of the insert may be cloned individually into non-essential regions (for example the polyhedrin gene) of the virus and placed under control of an AcNPV promoter (for example the polyhedrin promoter). Successful insertion of the coding sequence will result in inactivation of the polyhedrin gene and production of non-occluded recombinant virus (i.e., virus lacking the proteinaceous coat coded for by the polyhedrin gene). These recombinant viruses are then used to infect *Spodoptera frugiperda* cells in which the inserted gene is expressed. (for example, see Smith et al., *J. Virol.* 46:584, 1983; Smith, U.S. Pat. No. 4,215,051).

In mammalian host cells, a number of viral-based expression systems may be utilized. In cases where an adenovirus is used as an expression vector, the nucleic acid molecule of the invention may be ligated to an adenovirus transcription/translation control complex, for example, the late promoter and tripartite leader sequence. This chimeric gene may then be inserted in the adenovirus genome by in vitro or in vivo recombination. Insertion in a non-essential region of the viral genome (for example, region E1 or E3) will result in a recombinant virus that is viable and capable of expressing a MASP-2 gene product in infected hosts (for example, see Logan and Shenk, *Proc. Natl. Acad. Sci. USA* 81:3655–3659, 1984). Specific initiation signals may also be required for efficient translation of inserted nucleic acid molecules. These signals include the ATG initiation codon and adjacent sequences. In cases where an entire gene or cDNA, including its own initiation codon and adjacent sequences, is inserted into the appropriate expression vector, no additional translational control signals may be needed. However, in cases where only a portion of the coding sequence is inserted, exogenous translational control signals, including, perhaps, the ATG initiation codon, must be provided. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bittner et al., *Methods in Enzymol.* 153:516–544, 1987).

In addition, a host cell strain may be chosen which modulates the expression of the inserted sequences, or modifies and processes the gene product in the specific fashion desired. Such modifications (for example, glycosylation) and processing (for example, cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. The mammalian cell types listed above are among those that could serve as suitable host cells.

For long-term, high-yield production of recombinant proteins, stable expression is preferred. For example, cell lines which stably express the MASP-2 sequences described above may be engineered. Rather than using expression vectors which contain viral origins of replication, host cells can be transformed with DNA controlled by appropriate expression control elements (for example, promoter, enhancer sequences, transcription terminators, polyadenylation sites, etc.), and a selectable marker. Following the introduction of the foreign DNA, engineered cells may be allowed to grow for 1–2 days in an enriched media, and then switched to a selective media. The selectable marker in the recombinant plasmid confers resistance to the selection and allows cells to stably integrate the plasmid into their chromosomes and grow to form foci which in turn can be cloned and expanded into cell lines. This method can advantageously be used to engineer cell lines which express MASP-2. Such engineered cell lines may be particularly useful in screening and evaluation of compounds that affect the endogenous activity of the gene product and for production of MASP-2 for theraputic uses. These methods may also be used to modify cells that are introduced into a host organism either for experimental or theraputic purposes. The introduced cells may be transient or permanent within the host organism.

A number of selection systems can be used. For example, the herpes simplex virus thymidine kinase (Wigler, et al., *Cell* 11:223, 1977), hypoxanthine-guanine phosphoribosyltransferase (Szybalska and Szybalski, *Proc. Natl. Acad. Sci. USA* 48:2026, 1962), and adenine phosphoribosyltransferase (Lowy, et al., *Cell* 22:817, 1980) genes can be employed in tk⁻, hgprt⁻ or aprt⁻ cells, respectively. Also, anti-metabolite resistance can be used as the basis of selection for the following genes: dhfr, which confers resistance to methotrexate (Wigler et al., *Proc. Natl. Acad. Sci. USA* 77:3567, 1980; O'Hare et al., *Proc. Natl. Acad. Sci. USA* 78:1527, 1981); gpt, which confers resistance to mycophenolic acid (Mulligan and Berg, *Proc. Natl. Acad. Sci. USA* 78:2072, 1981); neo, which confers resistance to the aminoglycoside G-418 (Colbere-Garapin et al., *J. Mol. Biol.* 150:1, 1981); and hygro, which confers resistance to hygromycin (Santerre et al., *Gene* 30:147, 1984).

Alternatively, any fusion protein may be readily purified by utilizing an antibody specific for the fusion protein being expressed. For example, a system described by Janknecht et al. allows for the ready purification of non-denatured fusion proteins expressed in human cell lines (*Proc. Natl. Acad. Sci. USA* 88: 8972–8976, 1991). In this system, the gene of interest is subcloned into a vaccinia recombination plasmid such that the gene's open reading frame is translationally fused to an amino-terminal tag consisting of six histidine residues. Extracts from cells infected with recombinant vaccinia virus are loaded onto $Ni^{2+}$.nitriloacetic acid-agarose columns and histidine-tagged proteins are selectively eluted with imidazole-containing buffers.

MASP-2 Polypeptides

The MASP-2 polypeptides described herein are those encoded by any of the nucleic acid molecules described above and include MASP-2 fragments, mutants, truncated forms, and fusion proteins. These polypeptides can be prepared for a variety of uses, including but not limited to the generation of antibodies, as reagents in diagnostic assays, for the identification of other cellular gene products or compounds that can modulate the MBLectin response, and as pharmaceutical reagents useful for the treatment of inflammation and certain disorders (described below) that are associated with activity of of the MBLectin pathway. Preferred polypeptides are substantially pure MASP-2 polypeptides, including those that correspond to the polypeptide with an intact signal sequence (extending from amino acids 1–15 of SEQ ID NO:2), the mature form of the polypeptide (extending from amino acids 16–686 of SEQ ID NO:2) of the human MASP-2 polypeptide as well as polypeptides representing a part of the MASP-2 polypeptide. Especially preferred are polypeptides that are soluble under normal physiological conditions.

The invention also encompasses polypeptides that are functionally equivalent to MASP-2. These polypeptides are equivalent to MASP-2 in that they are capable of carrying out one or more of the functions of MASP-2 in a biological system. Preferred MASP-2 polypeptides have 20%, 40%, 50%, 75%, 80%, or even 90% of the activity of the full-length, mature human form of MASP-2 described herein. Such comparisons are generally based on an assay of biological activity in which equal concentrations of the polypeptides are used and compared. The comparison can also be based on the amount of the polypeptide required to reach 50% of the maximal activity obtainable.

Functionally equivalent proteins can be those, for example, that contain additional or substituted amino acid residues. Substitutions may be made on the basis of similarity in polarity, charge, solubility, hydrophobicity, hydrophilicity, and/or the amphipathic nature of the residues involved. Amino acids that are typically considered to provide a conservative substitution for one another are specified in the summary of the invention. D-amino acids may be introduced in order to modify the half-life of the polypeptide.

Polypeptides that are functionally equivalent to MASP-2 (SEQ ID NO:2) can be made using random mutagenesis techniques well known to those skilled in the art (and the resulting mutant MASP-2 proteins can be tested for activity). It is more likely, however, that such polypeptides will be generated by site-directed mutagenesis (again using techniques well known to those skilled in the art). These polypeptides may have an increased function, i.e., a greater ability to activate the MBLectin pathway. Such polypeptides can be used to enhance the activity of MBLectin pathway immune function.

To design functionally equivalent polypeptides, it is useful to distinguish between conserved positions and variable positions. This can be done by aligning the sequence of MASP-2 cDNAs that were obtained from various organisms. Skilled artisans will recognize that conserved amino acid residues are more likely to be necessary for preservation of function. Thus, it is preferable that conserved residues are not altered.

Mutations within the MASP-2 coding sequence can be made to generate MASP-2 peptides that are better suited for expression in a selected host cell. Introduction of a glycosylation sequence can also be used to generate a MASP-2 polypeptide with altered biological characteristics.

The invention also features methods for assay of polymorphisms within the polypeptide sequence comprising MASP-2 or its precursor. This may be accomplished by a number of techniques. For example, the purified polypeptide is subjected to tryptic digestion and the resulting fragments analyzed by either one-or two dimensional electrophoresis. The results from analysis of a sample polypeptide are compared to the results using a known sequence. Also the analysis may encompass separation of a biological sample (e.g., serum or other body fluids) by either one- or two-dimensional electrophoresis followed by transfer of the separated proteins onto a membrane (western blot). The membrane is then reacted with antibodies against MASP-2, followed by a secondary labelled antibody. The staining pattern is compared with that obtained using a sample with a known sequence or modification.

The polypeptides of the invention can be expressed fused to another polypeptide, for example, a marker polypeptide or fusion partner. For example, the polypeptide can be fused to a hexa-histidine tag to facilitate purification of bacterially expressed protein or a hemagglutinin tag to facilitate purification of protein expressed in eukaryotic cells. The MASP-2 polypeptide of the invention, or a portion thereof, can also be altered so that it has a longer circulating half-life by fusion to an immunoglobulin Fc domain (Capon et al., Nature 337:525–531, 1989). Similarly, a dimeric form of the MASP-2 polypeptide can be produced, which has increased stability in vivo.

The polypeptides of the invention can be chemically synthesized (for example, see Creighton, "Proteins: Structures and Molecular Principles," W. H. Freeman & Co., NY, 1983), or, perhaps more advantageously, produced by recombinant DNA technology as described herein. For additional guidance, skilled artisans may consult Ausubel et al. (supra), Sambrook et al. ("Molecular Cloning, A Laboratory Manual," Cold Spring Harbor Press, Cold Spring Harbor, N.Y., 1989), and, particularly for examples of chemical synthesis Gait, M. J. Ed. ("Oligonucleotide Synthesis," IRL Press, Oxford, 1984).

The invention also features polypeptides that interact with MASP-2 (and the genes that encode them) and thereby alter the function of MASP-2 interacting polypeptides can be identified using methods known to those skilled in the art. One suitable method is the "two-hybrid system," which detects protein interactions in vivo (Chien et al., *Proc. Natl. Acad. Sci. USA*, 88:9578, 1991). A kit for practicing this method is available from Clontech (Palo Alto, Calif.).

Anti-MASP-2 Antibodies

Human MASP-2 polypeptides (or immunogenic fragments or analogs) can be used to raise antibodies useful in the invention; such polypeptides can be produced by recombinant techniques or synthesized (see, for example, "Solid Phase Peptide Synthesis," supra; Ausubel et al., supra). In general, the peptides can be coupled to a carrier protein, such as KLH, as described in Ausubel et al., supra, mixed with an adjuvant, and injected into a host mammal. Also the carrier could be PPD. Antibodies can be purified by peptide antigen affinity chromatography.

In particular, various host animals can be immunized by injection with a MASP-2 protein or polypeptide. Host animals include rabbits, mice, guinea pigs, rats, and chickens. Various adjuvants that can be used to increase the immunological response depend on the host species and include Freund's adjuvant (complete and incomplete), mineral gels such as aluminum hydroxide, surface active substances such as lysolecithin, pluronic polyols, polyanions, peptides, oil emulsions, keyhole limpet hemocyanin, and dinitrophenol. Potentially useful human adjuvants include BCG (bacille Calmette-Guerin) and *Corynebacterium parvum*. Polyclonal antibodies are heterogeneous populations of antibody molecules that are contained in the sera of the immunized animals.

Antibodies within the invention therefore include polyclonal antibodies and, in addition, monoclonal antibodies, humanized or chimeric antibodies, single chain antibodies, Fab fragments, F(ab')$_2$ fragments, and molecules produced using a Fab expression library, and antibodies or fragments produced by phage display techniques.

Monoclonal antibodies, which are homogeneous populations of antibodies to a particular antigen, can be prepared using the MASP-2 proteins described above and standard hybridoma technology (see, for example, Kohler et al., Nature 256:495, 1975; Kohler et al., *Eur. J. Immumol.* 6:511, 1976; Kohler et al., *Eur. J. Immumol.* 6:292, 1976; Hammerling et al., "Monoclonal Antibodies and T Cell Hybridomas," Elsevier, N.Y., 1981; Ausubel et al., supra).

In particular, monoclonal antibodies can be obtained by any technique that provides for the production of antibody molecules by continuous cell lines in culture such as described in Kohler et al., Nature 256:495, 1975, and U.S. Pat. No. 4,376,110; the human B-cell hybridoma technique (Kosbor et al., *Immunology Today* 4:72, 1983; Cole et al., *Proc. Natl. Acad. Sci. USA* 80:2026, 1983), and the EBV-hybridoma technique (Cole et al., "Monoclonal Antibodies and Cancer Therapy," Alan R. Liss, Inc., pp. 77–96, 1983). Such antibodies can be of any immunoglobulin class including IgG, IgM, IgE, IgA, IgD and any subclass thereof. (In the case of chckens, the immunoglobulin class can also be IgY.) The hybridoma producing the mAb of this invention may be cultivated in vitro or in vivo. The ability to produce high titers of mabs in vivo makes this the presently preferred method of production, but in some cases, in vitro production will be preferred to avoid introducing cancer cells into live animals, for example, in cases where the presence of normal immunoglobulins coming from the acitis fluids are unwanted, or in cases involving ethical considerations.

Once produced, polyclonal, monoclonal, or phage-derived antibodies are tested for specific MASP-2 recognition by Western blot or immunoprecipitation analysis by standard methods, e.g., as described in Ausubel et al., supra. Antibodies that specifically recognize and bind to MASP-2 are useful in the invention. For example, such antibodies can be used in an immunoassay to monitor the level of MASP-2 produced by an animal (for example, to determine the amount or subcellular location of MASP-2).

Preferably, antibodies of the invention are produced using fragments of the MASP-2 protein which lie outside highly conserved regions and appear likely to be antigenic, by criteria such as high frequency of charged residues. In one specific example, such fragments are generated by standard techniques of PCR, and are then cloned into the pGEX expression vector (Ausubel et al., supra). Fusion proteins are expressed in *E. coli* and purified using a glutathione agarose affinity matrix as described in Ausubel, et al., supra.

In some cases it may be desirable to minimize the potential problems of low affinity or specificity of antisera. In such circumstances, two or three fusions can be generated for each protein, and each fusion can be injected into at least two rabbits. Antisera can be raised by injections in a series, preferably including at least three booster injections.

Antisera is also checked for its ability to immunoprecipitate recombinant MASP-2 proteins or control proteins, such as glucocorticoid receptor, CAT, or luciferase.

The antibodies can be used, for example, in the detection of the MASP-2 in a biological sample as part of a diagnostic assay. Antibodies also can be used in a screening assay to measure the effect of a candidate compound on expression or localization of MASP-2. Additionally, such antibodies can be used in conjunction with the gene therapy techniques described to, for example, evaluate the normal and/or engineered MASP-2-expressing cells prior to their introduction into the patient. Such antibodies additionally can be used in a method for inhibiting abnormal MASP-2 activity.

In addition, techniques developed for the production of "chimeric antibodies" (Morrison et al., *Proc. Natl. Acad. Sci. USA*, 81:6851, 1984; Neuberger et al., *Nature*, 312:604, 1984; Takeda et al., *Nature*, 314:452, 1984) by splicing the genes from a mouse antibody molecule of appropriate antigen specificity together with genes from a human antibody molecule of appropriate biological activity can be used. A chimeric antibody is a molecule in which different portions are derived from different animal species, such as those having a variable region derived from a murine mAb and a human immunoglobulin constant region.

Alternatively, techniques described for the production of single chain antibodies (U.S. Pat. Nos. 4,946,778, 4,946,778, and 4,704,692) can be adapted to produce single chain antibodies against a MASP-2 protein or polypeptide. Single chain antibodies are formed by linking the heavy and light chain fragments of the Fv region via an amino acid bridge, resulting in a single chain polypeptide.

Antibody fragments that recognize and bind to specific epitopes can be generated by known techniques. For example, such fragments include but are not limited to F(ab')$_2$ fragments that can be produced by pepsin digestion of the antibody molecule, and Fab fragments that can be generated by reducing the disulfide bridges of F(ab')$_2$ fragments. Alternatively, Fab expression libraries can be constructed (Huse et al., *Science*, 246:1275, 1989) to allow rapid and easy identification of monoclonal Fab fragments with the desired specificity.

Antibodies to MASP-2 can, in turn, be used to generate anti-idiotype antibodies that resemble a portion of MASP-2 using techniques well known to those skilled in the art (see, e.g., Greenspan et al., *FASEB J.* 7:437, 1993; Nissinoff, *J. Immunol.* 147:2429, 1991). For example, antibodies that bind to MASP-2 and competitively inhibit the binding of a ligand of MASP-2 can be used to generate anti-idiotypes that resemble a ligand binding domain of MASP-2 and, therefore, bind and neutralize a ligand of MASP-2 such as MBL. Such neutralizing anti-idiotypic antibodies or Fab fragments of such anti-idiotypic antibodies can be used in therapeutic regimens.

Antibodies can be humanized by methods known in the art. For example, monoclonal antibodies with a desired binding specificity can be commercially humanized (Scotgene, Scotland; Oxford Molecular, Palo Alto, Calif.). Fully human antibodies, such as those expressed in transgenic animals are also features of the invention (Green et al., Nature Genetics 7:13–21, 1994; see also U.S. Pat. Nos. 5,545,806 and 5,569,825, both of which are hereby incorporated by reference).

The methods described herein in which anti-MASP-2 antibodies are employed may be performed, for example, by utilizing pre-packaged diagnostic kits comprising at least one specific MASP-2 nucleotide sequence or antibody reagent described herein, which may be conveniently used, for example, in clinical settings, to diagnose patients exhibiting symptoms of the disorders described below.

Quantitative Assays of MASP-2

As an example only, quantitative assays may be devised for the estimation of MASP-2 concentrations in body fluids or organ (biopsy) extracts. Such assays may be fluid phase or solid phase. Examples are competitive and non-competitive ELISAs. As an example of the latter, microtiter wells are coated with anti-MASP-2 antibody, incubated with samples, and the presence of MASP-2 visualized with enzyme-labelled antibody followed by substrate that deposits a colored compound. Alternatively, a label such as europium may be used and the detection made by use of time resolved fluorometry.

Assays of the functional activity of MASP-2, either alone or as part of the MBL/MASP complex may be performed by several methods. As an example of a test for MBL/MASP-2 complex, the test sample is applied onto mannan-coated micro wells and C4 is added to estimate the C4-cleaving activity, or C3 is added to estimate the C3 cleaving activity of the generated C3 convertase. Assay of MASP-2 not occurring as part of the MBL/MASP complex is carried out similarly, but MBL is added either to the micro well or to the sample before adding this to the mannan-coated well. Before the addition of MBL the sample may be depleted of MBL and MBL/MASP-1 and MBL/MASP-2 complexes by treatment with solid phase mannan, e.g. attached to beads, or by solid phase anti-MBL antibodies, or by treatment with a suitable concentration of a precipitating agent, e.g., PEG, which precipitates the complex but leaves MASP-2 in the supernatant. The assay is carried out at conditions which minimize or eliminate interference from the classical complement activation pathway and the alternative complement activation pathway.

Assays estimating the activity of MASP-2 or MASP-2 may be used for diagnostic and treatment purposes in samples from individuals, notably those suffering from infectious or inflammatory diseases.

MASP-2 for Therapy

Therapeutic use of components specified in the claims may be applied in situations where a constitutional or temporary deficiency in MASP-2 renders the individual susceptible to one or more infections, or situations where the individual cannot neutralize an established infection. MASP-2 or MBL/MASP complexes can be administered, preferably by intravenous infusions, in order to improve the individual's immune defense.

We believe MASP-2 is required for the powerful antimicrobial activity of the MBL/MASP complex, and deficiency in MASP-2, either genetically determined or acquired, will therefore compromise an individual's resistance to infections and ability to combat established infections. Reconstitution with natural or recombinant MASP-2 is a useful treatment modality in such situations. Recombinant MASP-2 may be in the form of the whole molecule, parts of the molecule, or the whole or part thereof attached by any means to another structure in order to modulate the activity. The recombinant products may be identical in structure to the natural molecule or slightly modified to yield enhanced activity or decreased activity when such is desired.

Reconstitution therapy with MBL, either natural or recombinant, requires that the recipient has sufficient MASP-2 for the expression of MBL/MASP activity. Thus, MASP-2 must be included in the therapeutic preparation when the patient has insufficient MASP-2 activity.

Assays for MASP-2

Therapy with MASP-2 (or MASP-2 inhibitors) must usually be preceded by the estimation of MASP-2 in serum or plasma from the patient. Examples of such assays are described below.

Assays for MASP-2 Antigen

MASP-2 protein is conveniently estimated as antigen using one of the standard immunological procedures.

As an example only, a quantitative TRIFMA (time resolved immunofluorometric assay) for MASP-2 was constructed by 1) coating microtitre wells with 1 µg anti-C'

MASP-2 antibody; 2) blocking with Tween-20; 3) applying test samples, e.g. diluted plasma or serum samples: 4) applying Eu-labelled anti-N' MASP-2 antibody; 5) applying enhancement solution (Wallac Ltd): 6) reading the Eu on a time resolved fluorometer. (Estimation by ELISA may be carried out similarly, e.g. by using biotin-labelled anti-N' MASP-2 in step 4; alkaline phosphatase-labelled avidin in step 5; 6) apply substrate; and 7) read the colour intensity.) Between each step, the plate was incubated at room temperature and washed, except between step 6 and 7. A calibration curve may be constructed using dilutions of pooled normal plasma, arbitrarily said to contain 1 unit of MASP-2 per ml. The antibodies used in this first version of a MASP-2 assay were raised against synthetic peptides and reacted poorly with native MASP-2. The samples are thus pretreated with SDS on a boiling water bath for 5 min. and the SDS neutralized with non-ionic detergent (Triton X-100) before the assay. A further development of the assay employs antibodies reacting with native MASP-2, thus rendering the SDS treatment superfluous.

Assays may be similarly constructed using antibodies, polyclonal or monoclonal or recombinant antibodies, which reacts with MASP-2, natural or recombinant, or parts thereof.

Through the use of antibodies reacting selectively with intact MASP-2 or with activation products, or through combination of antibodies against various parts of the molecule, assays may be constructed for the estimation of the activation in vivo of the MBLectin pathway. These assays will be useful for the determination of inflammation caused by the activation of this pathway.

Assays for MASP-2 Activity of the MPL/MASP Complex.

MASP-2 may be estimated by its capacity to activate the complement system. When C4 is cleaved by MASP-2 an active thiol ester is exposed and C4 becomes covalently attached to nearby nucleophilic groups. A substantial part of the C4b will thus become attached to the coated plastic well and may be detected by anti-C4 antibody. A quantitative TRIFMA for MASP-2 activity was constructed by 1) coating microtiter wells with 1 $\mu$g mannan in 100 $\mu$l buffer; 2) blocking with Tween-20; 3) applying test samples, e.g. diluted plasma or serum samples: 4) applying purified complement factor C4 at 5 $\mu$g/ml; 5) incubate for one hour at 37° C.; 6) applying Eu-labelled anti-C4 antibody; 7) applying enhancement solution; and 8) reading the Eu by time resolved fluorometry. (Estimation by ELISA may be carried out similarly, e.g. by applying biotin-labelled anti-C4 in step 6; 7) apply alkaline phosphatase-labelled avidin; 8) apply substrate; and 9) read the colour intensity). Between each step the plate was incubated at room temperature and washed, except between step 7 and 8. A calibration curve can be constructed using dilutions of one selected normal plasma, arbitrarily said to contain 1 unit of MBL/MASP-2 activity per ml. The assay is carried out at conditions which preclude activation of C4 by the classical or alternative complement activation pathways. The activation of C4 was completely inhibited by the serine protease inhibitor benzamidine. Activation of the classical pathway is effectively eliminated by carrying out step 3) in the presence of sufficiently high ionic strength (0.7 to 2.0 NaCl; preferably about 1.0 M NaCl) which does not interfere with the MBL/MASP complex but completely destroys the C1qrs complex; activation of the alternative pathway is effectively precluded by assaying at a dilution of 20-fold or greater.

Assays for the Estimation of Free MASP-2 Activity

The estimation of MASP-2 activity in samples from MBL-deficient individuals is carried out on wells coated with MASP-free MBL. The estimation of free MASP in samples from individuals with MBL is carried out by first removing MBL/MASP-1 and MBL/MASP-2 complexes by incubating with Sepharose-coupled mannan (300 $\mu$l of 10 fold diluted plasma or serum is incubated with 10 $\mu$l beads), and then analyzing the supernatant.

The assay carried out in the TRIFMA formate proceeds as follows: 1) coating microtiter wells with 1 $\mu$g mannan in 100 $\mu$l buffer; 2) blocking with Tween-20; 3) incubate sample at a 1000 fold dilution in buffer with 100 ng of MASP-free MBL/ml, and applying 100 $\mu$l of the mixture per well; 4) incubate over night at 4° C.; 4) wash and applying purified complement factor C4 at 5 $\mu$g/ml; 5) incubate for one hour at 37° C.; 6) applying Eu-labelled anti-C4 antibody; 7) applying enhancement solution; and 8) reading the Eu by time resolved fluorometry. (Estimation by ELISA may be carried out similarly, e.g. by applying biotin-labelled anti-C4 in step 6; 7) apply alkaline phosphatase-labelled avidin; 8) apply substrate; and 9) read the colour intensity.) Between each step the plate was washed, except between step 7 and 8. A calibration curve may be constructed using dilutions of one selected MBL-deficient plasma, arbitrarily said to contain 1 unit of MASP-2 activity per ml. The assay is carried out at conditions which preclude activation of C4 by the classical or alternative complement activation pathways (see above).

Inhibition of MASP-2 Activity

Inhibitors of the biological activity of MASP-2 may be employed to control the complement activating activity and inflammatory activity of MASP-2. Such inhibitors may be substrate analogues representing target structures of C2 or C4. Inhibitors may be of peptide nature, modified peptides, or any organic molecule which inhibits the activity of MASP-2 competitively or non-competitively. The inhibitor may be modified to stay in circulation for short or longer time, and constructed to be given by injection or perorally. Inhibitors may be fragments of MASP-2, produced from natural or recombinant MASP-2, by chemical or enzymatic procedures. Inhibitors may be naturally occurring shorter forms of MASP-2. Inhibitors may be in soluble form or coupled to a solid phase. A solid phase could be a compatible surface such as used in extracorporal blood or plasma flow devices.

Microbial carbohydrates or endogenous oligosaccharides may provoke undesirable activation of the MBL/MASP complex resulting in damaging inflammatory responses. This pathophysiological activity may be reduced though the administration of inhibitors of MASP-2 activity such as Pefabloc. Also other enzyme inhibitors (PMSF, benzamidine, etc.) have proved effective when assayed in the TRIFMA for MASP-2 activity. Obviously, when designing inhibitors for in vivo use toxicity is a major consideration, and highly specific inhibitors can be assumed to be less toxic than more broadly reactive inhibitors. Specific inhibitors may be generated through using peptides, peptide analogues or peptide derivatives representing the target structures on complement factor C4 or C2 molecules. Another type of inhibitors may be based on antibodies (or fragments of antibodies) against the active site of MASP-2 or other structures on MASP-2 thus inhibiting the activity of MASP-2. Inhibitors may also be directed towards inhibition of the activation of MASP-2, thought to be effected by MASP-1, i.e. the target structure for MASP-1 on MASP-2 would be a suitable inhibitor of this type. Another type of inhibitor would prevent the binding of MASP-2 to MBL and thereby the activation of MASP-2. The N-terminal 20 kDa fragment of MASP-2 may be a suitable inhibitor of this type.

More specifically one can localize the precise part of the polypeptide chain which mediates the binding of MASP-2 to MBL and use the synthetic peptide or analogous structures as inhibitor. Inhibitors may be substituted with D amino acids for L-amino acids.

Also, inhibitors could be RNA or single stranded DNA isolated by SELEX (systemic evolution of ligands by exponential enrichment) using MASP-2 or fragments thereof as selecting molecule. The leader sequence of MASP-2 is shown elsewhere in this application.

MASP-2 activity may be controlled by the conversion of the pro-enzyme form of MASP-2 into activated MASP-2 through the action of MASP-1 or any other substance simulating the activity of MASP-1.

EXAMPLES

Example 1
Identification of MASP-2

Human plasma proteins and protein complexes, that bind to carbohydrates in a calcium-dependent manner (i.e. lectins and lectin-associated proteins), were purified by affinity chromatography on mannan- and N-acetylglucosamine-derivatized Sepharose beads. Pooled CPD-plasma (2.5 l), diluted with buffer containing EDTA and enzyme inhibitors were passed through Sepharose 2B CL and mannan-Sepharose. A thrombin inhibitor, PPACK (D-phenylalanyl-prolyl-arginyl-chloromethyl ketone) and $CaCl_2$ were added. The pool was passed through Sepharose 2B-CL and mannan-Sepharose, and the proteins binding calcium-dependently to mannan-Sepharose were eluted with EDTA-containing buffer. The eluate was recalcified, passed through a GlcNAc-Sepharose column which was eluted as above to yield 20 ml "lectin preparation".

Figure 6:
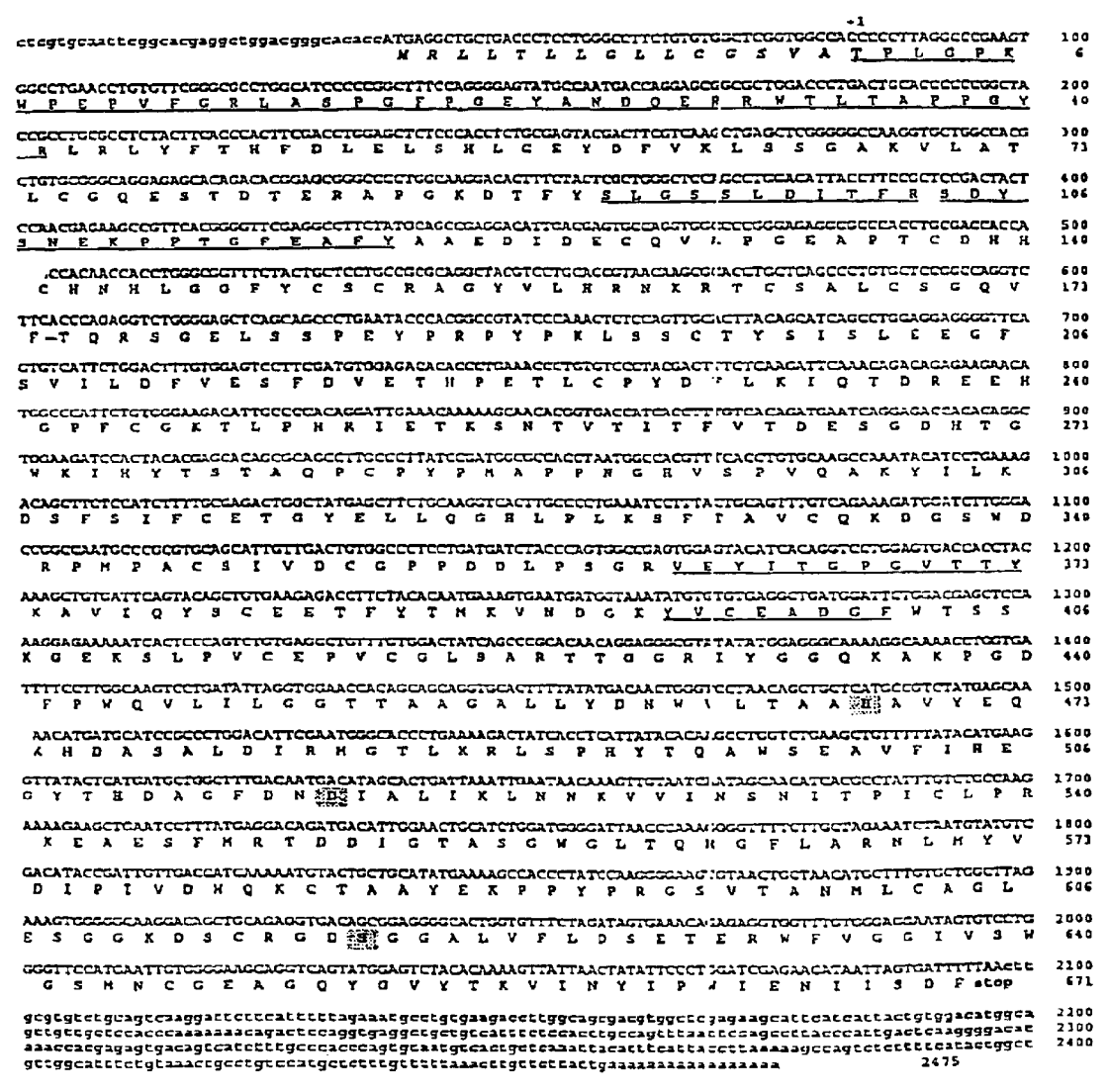

This protein preparation was analyzed by SDS-PAGE and blotting onto a PVDF-membrane. Development of the blot with chicken antibody raised against a bovine lectin preparation[25] revealed a protein with an $M_r$ of 52 kDa as well as MBL at 32 kDa. The 52 kDa band was subjected to $NH_2$-terminal amino acid sequence analysis. The sequence showed similarity to that of the previously described MASP (MASP-1). Antibody raised against a synthetic peptide representing the 19 $NH_2$-terminal amino acids (anti-N' MASP-2 antiserum) recognized the 52 kDa molecule as well as a molecule with a mobility corresponding to 20 kDa (FIG. 1, lane 1). Under non-reducing conditions a polypeptide of 76 kDa was detected using the anti-N'-MASP-2 antiserum (FIG. 1, lane 2), indicating the presence of intra-chain disulphide bonds. The 20 kDa polypeptide was found to have the same $NH_2$-terminal sequence as the 52 kDa polypeptide and is likely to represent a truncated form of the latter. The directly determined amino acid sequences ($NH_2$-terminal as well as those of internal peptides) are indicated in FIG. 6. Two dimensional SDS-PAGE with the first dimension under nonreducing conditions and the second dimension under reducing conditions showed the 52 kDa polypeptide to be part of a disulphide-linked protein with an $M_r$ of 76 kDa. A polypeptide of 31 kDa (FIG. 1, lane 3), likely to represent the remaining part of the protein, was also recognized as part of the 76 kDa protein by an antiserum (anti-C' MASP-2) raised against synthetic peptides representing sequences in the COOH-terminal part of the protein (determined by cDNA sequencing techniques; see below). The 76 kDa band seen with the anti-N' MASP-2 antibody under non-reducing conditions was also recognized by the anti-C' MASP-2 antibody (FIG. 1, lane 4).

Figure 1A:
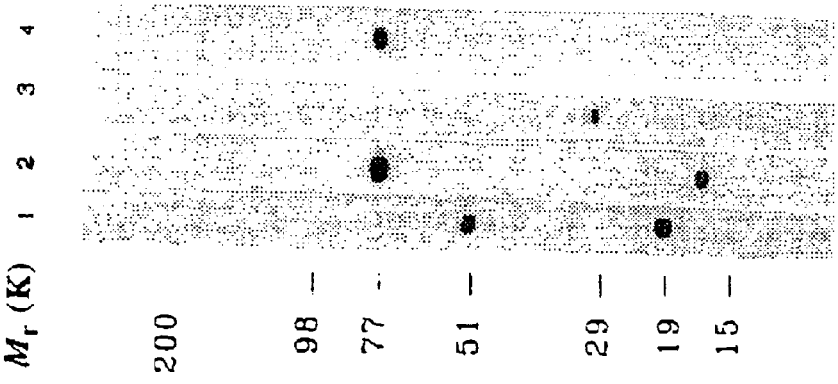

FIG. 1b depicts SDS-PAGE in two dimensions, the first dimension under non-reducing conditions. The lane was cut out, incubated in sample buffer containing dithiothreitol (DTT), placed on top of another SDS-PAGE gel, and after electrophoresis, the gel was blotted and the blot developed with anti-N' MASP-2 antibody. The positions of molecular weight markers are indicated.

Example 2
Preparation of Antibodies Against Mamman-binding Lectin Associated Serine Proteases Animals, primed with BCG (*Bacillus* Calmette Gurin vaccine) were immunized with synthetic peptides coupled to PPD (tuberculin purified protein derivative) according to C. Koch, The State Serum Institute, Copenhagen. Antibody designated anti-N' MASP-1, anti-C' MASP-1 and anti-N' MASP-2 were from rabbits immunized with peptides corresponding to the first 19 amino acid residues of MASP-1 (SEQ ID NO:6), the last 19 amino acid residues of MASP-1 (SEQ ID NO:6) and the first 19 amino acid residues of MASP-2 (SEQ ID NO:2), respectively. Chicken anti-C' MASP-2 antibody was from chickens immunized with a mixture of two peptides representing sequences in the C-terminal part of MASP-2 (residues 505 to 523 and 538 to 556). All peptides had an additional C-terminal cysteine for coupling. Antibody and normal chicken IgG was purified from yolk[26]. Monoclonal anti-MBL antibody, $IgG_1$-kappa (clone 131-1) and control $IgG_1$-kappa (clone MOPC 21) were purified by Protein A affinity chromatography. $F(ab')_2$ rabbit anti-human C4 and $F(ab')_2$ rabbit anti-human C1q were produced by pepsin digestion of rabbit anti-human C4 and rabbit anti-human C1q (DAKO, Glostrup, Denmark). For staining of Western blots antibodies were used at 1 µg/ml. Bound chicken antibody was visualized with rabbit anti-chicken IgG followed by peroxidase-labelled goat anti-rabbit IgG and development using the enhanced chemiluminescence technique. Bound mouse and rabbit antibodies were visualized with peroxidaselabelled rabbit anti-mouse IgG and peroxidase-labelled goat anti-rabbit IgG, respectively.

Example 3
Amino Acid Sequencing of the 52 kDa and the 20 kDa Polypeptides

The lectin preparation was concentrated, subjected to SDS-PAGE, and transferred to a PVDF membrane. Two strips were developed with anti-bovine lectin antibody[25]. The rest of the blot was stained with Coomassie Brilliant Blue. The band corresponding to the immuno-stained 52 kDa band, judged to represent about 5% of the total Coomassie-stained proteins, was cut out and subjected to sequencing on an Applied Biosystems protein sequencer. After production of anti-N' MASP-2 antibody, a similar Western blot was performed using the anti-N-MASP-2 antibody. The $NH_2$-termini of the proteins in the 52 kDa and the 20 kDa bands visualized with this antibody were sequenced. Peptides were prepared by trypsin digestion of the proteins in the two bands from another blot, fractionated by reverse phase chromatography and the peptides in the major peaks were subjected to sequencing.

Example 4
Cloning and Sequencing of MASP-2

The liver is the primary site of synthesis of C1r, C1s, and MASP-1. Thus, RNA from liver was used as template for RT-PCR with primers deduced from the obtained peptide sequences. First strand synthesis of cDNA was carried out with 1.3 µg human liver RNA using a First-Strand cDNA Synthesis Kit (Pharmacia). PCR was performed on this cDNA using degenerate sense and antisense primers derived from the amino acid sequences EYANDQER (SEQ ID NO: 4) and KPFTGFEA (SEQ ID NO:5), respectively. The PCR program consisted of 1 cycle with annealing at 50° C.; 1 cycle with annealing at 55° C., and 33 cycles with annealing at 60° C. The resulting 300 bp PCR product was cloned into the E. coli plasmid PCRII using the TA-cloning kit (InVitrogen) and the nucleotide sequence of the insert was determined.

The nucleotide sequence of the resulting 300 bp RT-PCR product contained an open reading frame (ORF) with a deduced amino acid sequence confirming the sequences of the peptides from which the primers were derived as well as that of another of the sequenced peptides. The insert of this plasmid was radioactivly labelled and used as a probe for screening a total of $8 \times 10^5$ clones in a commercial human liver library (Stratagene). Sixteen clones hybridized and the 4 longest (phl-1, 2, 3 and 4) were completely sequenced. Sequence analysis revealed that all four clones represent reverse transcripts of the same novel human mRNA species. The longest clone, phl-4, comprises 2475 bp starting with a 5' untranslated region of 36 bp followed by an ORF of 2061 bp and a 3' untranslated region of 378 bp ending with a poly-A tail. The nucleotide sequence (SEQ ID NO:3) of phl-4 is shown in FIG. 6 together with the translated amino acid sequence (SEQ ID NO:2). The sequences are deposited at the EMBL nucleotide sequence data base (accession no. Y09926). While the sequence of phl-1 and -2 were in total agreement with phl-4, the nucleotide sequence of phl-3 differs from phl-4 at two positions, a transversion at nucleotide position 1147 (G to T) and a transition at position 1515 (C to T). The first change leads to the replacement of Asp 356 with Tyr. Because all clones were isolated from a liver library transcribed from RNA isolated from a single donor, the observed difference may represent a polymorphism in the MASP-2 gene, or is due to an error created during construction of the library.

The amino acid sequences of the $NH_2$-terminus as well as all sequenced peptides were identified in the sequence deduced from clone phl-4. The ORF encodes a polypeptide chain of 686 amino acids (SEQ ID NO:2) including a signal peptide of 15 residues. Omitting the signal peptide, the calculated $M_r$ is 74,153, in agreement with the 76 kDa observed on SDS-PAGE (FIG. 1), the isoelectric point is 5.43 and the molar extinction coefficient is 113,640 (i.e. $OD_{280\,nm}$ =1.54 at 1 mg/ml). In contrast to MASP-1 (SEQ ID NO:6) the sequence contains no sites for N-linked glycosylation. The three amino acid residues which are essential for the active centre in serine proteases (His 468, Asp 517, and Ser 618) are present.

Example 5
Comparison of MASP-2 to MASP-1, C1r and C1s

Figure 2:
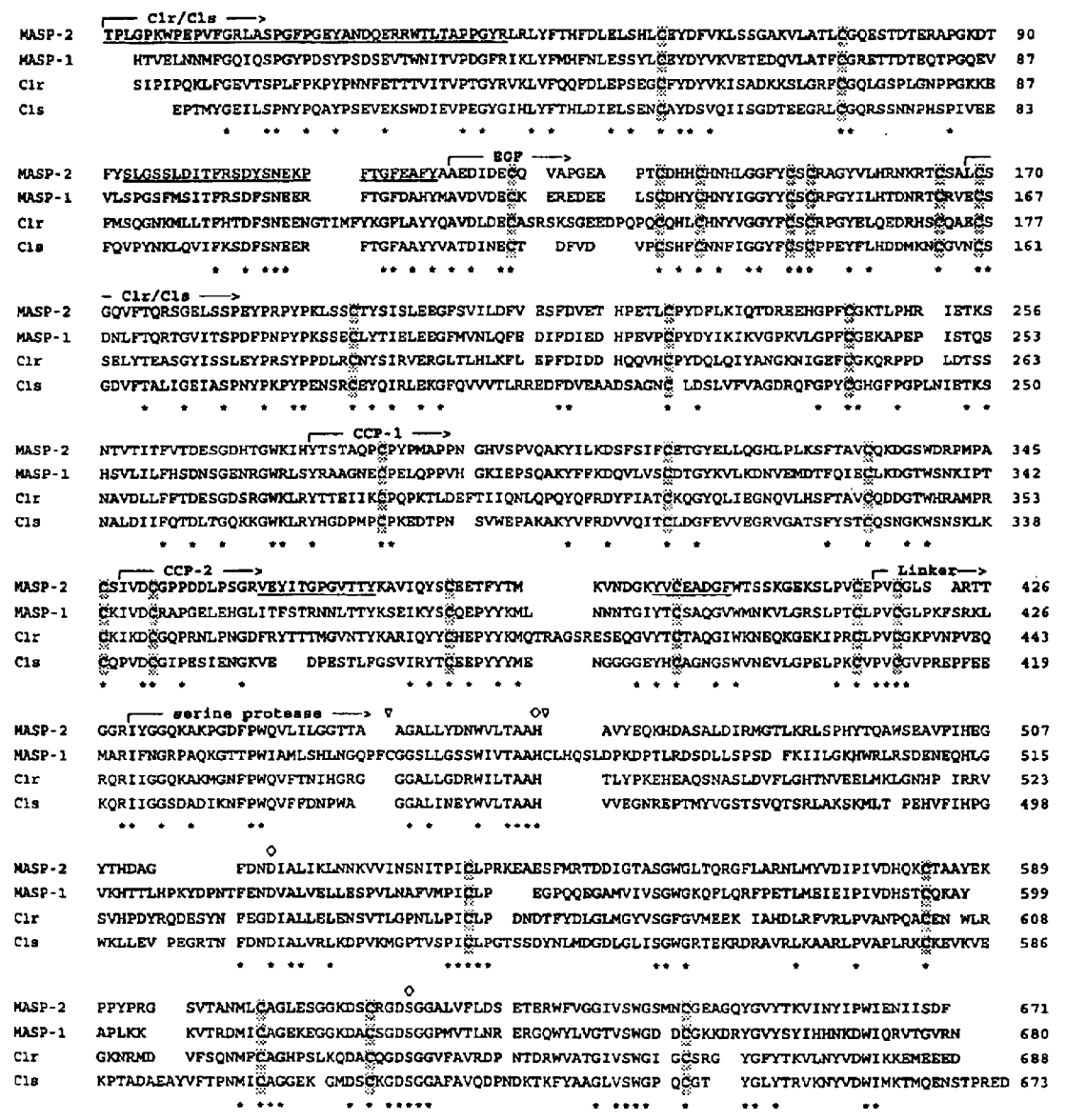

The amino acid sequence deduced from the cDNA sequences is homologous to those of MASP-1 (SEQ ID NO:6), C1r (SEQ ID NO:7) and C1s (SEQ ID NO:8) (FIG. 2). Notably, the domain organization is common to these four proteins, featuring one C1r/C1s-like domain, one epidermal growth factor-like (EGF-like) domain, followed by a second C1r/C1s-like domain, two complement control protein (CCP) domains, and a serine protease domain. The key residues involved in the calcium-binding motif in the epidermal growth factor-like domains are present in the obtained sequence (SEQ ID NO:2), as well as in MASP-1 (SEQ ID NO:6), C1r (SEQ ID NO:7) and C1s (SEQ ID NO:8) In addition, the substrate specificity related residue, 6 residues before the active site serine, is aspartic acid in all four proteins. MASP-1, C1r, and C1s are all activated by cleavage of the peptide bond between the residues Arg and Ile located between the second CCP domain and the serine protease domain. The resulting polypeptide chains (the largest referred to as the "heavy chain" and the smallest as "light chain") are held together by a disulphide bond. By analogy, our results indicate that the 52 kDa polypeptide, recognized by antibody against the N-terminal of MASP-2 after SDS-PAGE under reducing conditions, is the heavy chain of MASP-2, whereas the 31 kDa polypeptide, recognized by antibody against the C-terminal of MASP-2, is the light chain. As seen in FIG. 2, Arg and Ile are present in MASP-2 (SEQ ID NO:2) at the expected positions between the second CCP domain and the protease domain.

Identities and similarities between the four proteins were studied based on the alignment in FIG. 2. A bias of 6 was added to each term of the mutation data matrix (250 PAMS) arid a break penalty of 6 was used. Identical residues in all four species are indicated by asterisks. The beginning of the C1r/C1s-like domains, the EGF-like domain and the CCP domains are indicated above the sequences. The aligned cysteines are shaded. The potential cleavage site between Arg and Ile residues, which generates heavy and light chains, is identical to the site where the serine protease domain starts. The three amino acid residues, which are essential for the active centre in serine proteases (His 468, Asp 517 and Ser 618), are indicated ($\Diamond$). The cysteines in the histidine-loop of MASP-1 (SEQ ID NO:6) are marked ($\nabla$). The sequences obtained by amino acid sequencing of peptides are underlined. The identities between the proteins (FIG. 2) are all in the range of 39% to 45% and gives no clue to functional relatedness. The similarity, i.e. taking into account residues of similar nature as well as identical residues, between the proteins (FIG. 3b) are between 39 and 52% with the least similarity being between MASP-1 (SEQ ID NO:6) and C1s (SEQ ID NO:8) (39%) and the highest similarity between MASP-1 (SEQ ID NO:6) and C1r (SEQ ID NO:7) (52%) and between MASP-1 (SEQ ID NO:6) and MASP-2 (SEQ ID NO:2) (52%). MASP-2 (SEQ ID NO:2) shows similarity with C1r (46%) (SEQ ID NO:7) and C1s (47%) (SEQ ID NO:8). Whereas the relative identities gives no clue as to functional relatedness the similarity score between C1s and MASP-2 is significantly higher than between C1s and MASP-1 while MASP-1 is more similar to C1r than to C1s, suggesting that MASP-2, like C1s, could be a C2 and C4 cleaving enzyme. Several features of the sequences suggest that MASP-2, C1r and C1s have evolved by gene duplication and divergence from a MASP-1 ancestor. Only the MASP-1 (SEQ ID NO:6) sequence contains the histidine loop, characteristic of trypsin-like serine proteases[27]. The active site serine is encoded by a TCN codon (N is A, T, G or C) in MASP-1 as in most serine proteases, whereas in MASP-2 (SEQ ID NO:2), C1r (SEQ ID NO:7) and C1s (SEQ ID NO:8) it is encoded by an AGY codon (where Y is T or C). In most serine proteases, including MASP-1 (SEQ ID NO:6), a proline residue is found at the third position downstream from the active site serine, whereas a different amino acid is found in MASP-2 (SEQ ID NO:2), C1s (SEQ ID NO:8) and C1r (SEQ ID NO:7) (alanine in MASP-2 and C1s, valine in C1r). Based on these analogies one may predict that the catalytic domain of MASP-2 is encoded by a single exon as in C1r and C1s, whereas most other serine proteases, including MASP-1[28] (SEQ ID NO:6), have split exons.

Example 6
MBL/MASP Complexes

The lectin preparation described above was incubated in microtiter wells coated with monoclonal anti-MBL antibody, or, as a negative control, wells coated with non-specific monoclonal immunoglobulin of the same subclass. The proteins captured by the antibody were eluted and analyzed by SDS-PAGE/Western blotting. The results (FIG. 3a) show that the anti-MBL antibody, in addition to binding MBL, captures both MASP-1 and MASP-2. Microtite wells were coated with monoclonal anti-MBL or control monoclonal murine IgG1, incubated with either one of two different lectin preparations (a and b), and the bound proteins were eluted and analysed by SDS-PAGE under reducing conditions and Western blotting. Blot a was developed with anti-MBL antibody, blot b with anti-C' MASP-1 antibody and blot c with anti-N' MASP-2 antibody. Lane 1 represents unfractionated lectin preparation a. Lanes 3 and 4 represent eluates from wells coated with anti-MBL antibody and incubated with lectin preparation b and a, respectively, while lanes 2 and 5 represent eluates from wells coated with normal IgG and incubated with lectin preparation b and a, respectively.

Figure 3A:
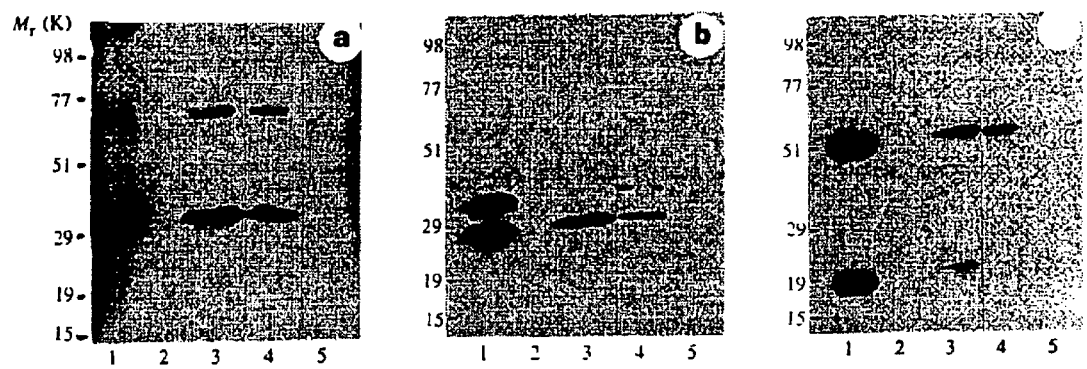
FIGS. 3a–3b are representations of the results demonstrating molecular complexes formed between MBL, MASP-1 and MASP-2.
Figure 3B:
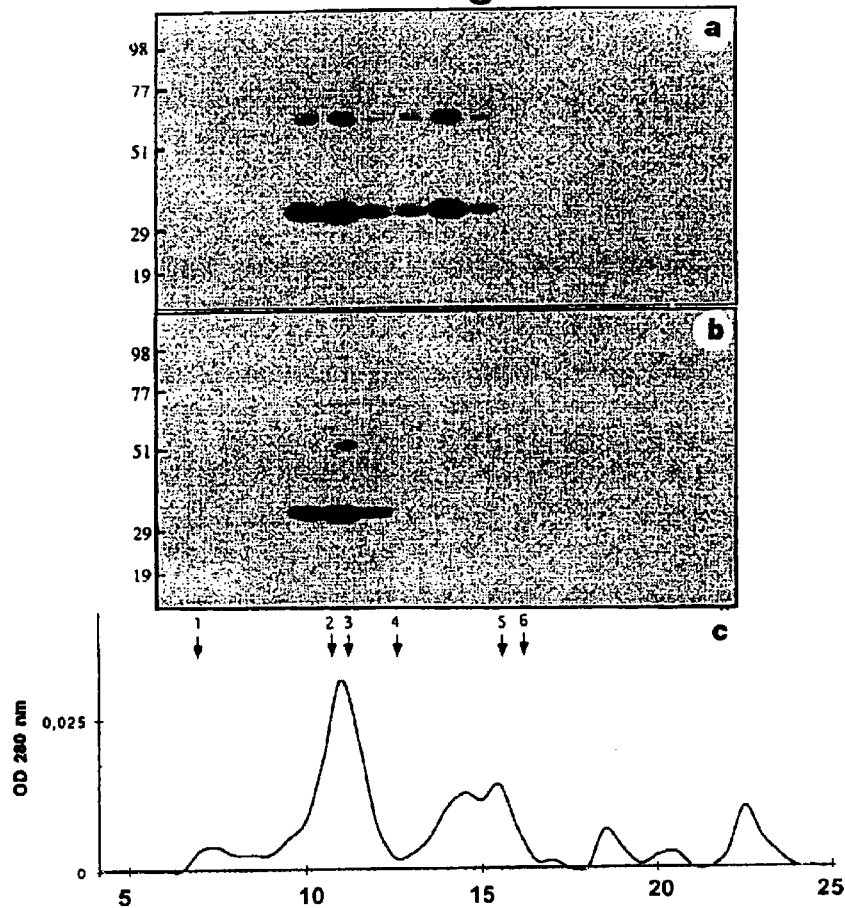

Fractions from gel permeation chromatography (GPC) of the lectin preparation on Superose 6B CL were analyzed for MBL, MASP-1 and MASP-2 (FIG. 3a). The lectin preparation was subjected to GPC on a Superose 6 column in buffer containing calcium. MBL was eluted in a main peak at a volume ($V_e$) corresponding to an $M_r$ of 750 kDa, and a smaller peak at a position corresponding to 350 kDa. Panel A shows the results of analysis of the fractions by Western blotting using monoclonal anti-MBL antibody. The band at about 60 kDa is seen in all MBL preparations and is recognized by all the anti-MBL antibodies tested (monoclonal as well as polyclonal) and thus probably represents a non-reducible dimer of the 32 kDa polypeptide chain. Panel B shows the same analysis using anti-N' MASP-2 antibody (developing the upper band of 52 kDa) followed by anti-C' MASP-1 antibody (developing the lower band of 31 kDa). For purely technical reasons the 20 kDa truncated MASP-2 is not seen in this picture where the blot was partially stripped between the incubations with anti-MASP-2 and anti-MASP-1. The arrows on the chromatogram indicate the void volume (1) and the elution positions for the following marker proteins IgM (2), C1q (3), thyroglobulin (4), IgG (5) and serum albumin (6).

Masp-1 and MASP-2 coelute largely with the high molecular weight MBL. Chromatography of the MBL preparation at pH 5 revealed that no MASP-1 or MASP-2 was associated with MBL. See, Tan et al. (1996, Biochem J. 319: 329–332).

Example 7
Complement Activation

The classical complement activation pathway, as well as the MBL-initiated pathway involves the generation of a C3 converting complex, C4b2b, through enzymatic activation of C4 and C2. In the C1 complex (C1qr$_2$s$_2$) this specific protease activity is exhibited by C1s after activation of the enzyme by C1r. Upon activation of C4, a reactive thiol ester is exposed and C4b covalently binds to nearby amino or hydroxyl groups.

The C4 activating potentials of MASP-1 and MASP-2, and C1r and C1s, were compared. This was accomplished by separating a C1 preparation and an MBL/MASP preparation by SDS-PAGE followed by Western blotting. The blot was examined for C4 converting activity by incubation with human serum at 37° C., followed by detection of deposited C4b using anti-C4 antibodies.

C1 was purified by incubating IgG-coupled Sepharose beads with human serum at 4° C. The beads were washed and incubated at 37° C. for 30 minutes for activation of C1r and C1s. The beads were suspended in non-reducing sample buffer and, without boiling, subjected to SDS-PAGE, followed by blotting in the absence of SDS. A similar blot was made of an MBL preparation produced in the absence of enzyme inhibitors (The State Serum Institute, Copenhagen). Strips of the blots were incubated for 30 minutes at 37° C. with 1.1% (v/v) human MBL-deficient serum, depleted of C1q by fractionation on Biorex 70. The blots were developed with biotinylated F(ab')$_2$ anti-C4 antibody followed by peroxidase-labelled streptavidin and luminescence reagent. Parallel blots were treated with a serine protease inhibitor (aminoethylbenzenesulfonyl fluoride), which was also present during incubation with serum. Other strips were directly developed with antibodies.

The results in FIG. 4 show that C4 was deposited at a position corresponding to the MASP-2 band, whereas no C4 deposition was observed at positions corresponding to MASP-1. MASP-1 was present in the activated state as shown by SDS-PAGE under reducing conditions where it appears as two bands at about 30 kDa and 70 kDa, respectively (not shown). The observed C4 activation and deposition was inhibited by serine protease inhibitors (FIG. 4). It was also observed that no C4 activating activity could be detected when MBL/MASP was prepared in the presence of enzyme inhibitors added throughout the purification procedure. A preparation of C1 was analyzed similarly and C4 deposition, which could be inhibited by enzyme inhibitors, was observed at a position corresponding to C1r and C1s, which are not separated by the technique employed.

FIG. 4 is a representation of Western blots demonstrating the activation of C4 by C1s and MASP-2. Panel A shows a Western blot of C1 separated under non-reducing conditions, and without heating the sample before electrophoresis. Lane 1 was developed with anti-C1s antibody. Lane 2 was incubated with human serum followed by anti-C4 antibody. Lane 3 was as lane 2 except for the presence of serine protease inhibitors during the incubation with serum. Panel B shows a Western blot of an MBL preparation separated as in A. Lane 1 was developed with anti-N' MASP-1, lane 2 with anti-N' MASP-2. Lane 3 was incubated with human serum at 37° C. followed by anti-C4. In lane 4 the blot was preincubated with serine protease inhibitors and the incubation with serum was also in the presence of inhibitors. MASP-1 shows a higher $M_r$, than MASP-2 due to glycosylation[17] and a polypeptide chain 9 amino acids longer.

Figure 5:
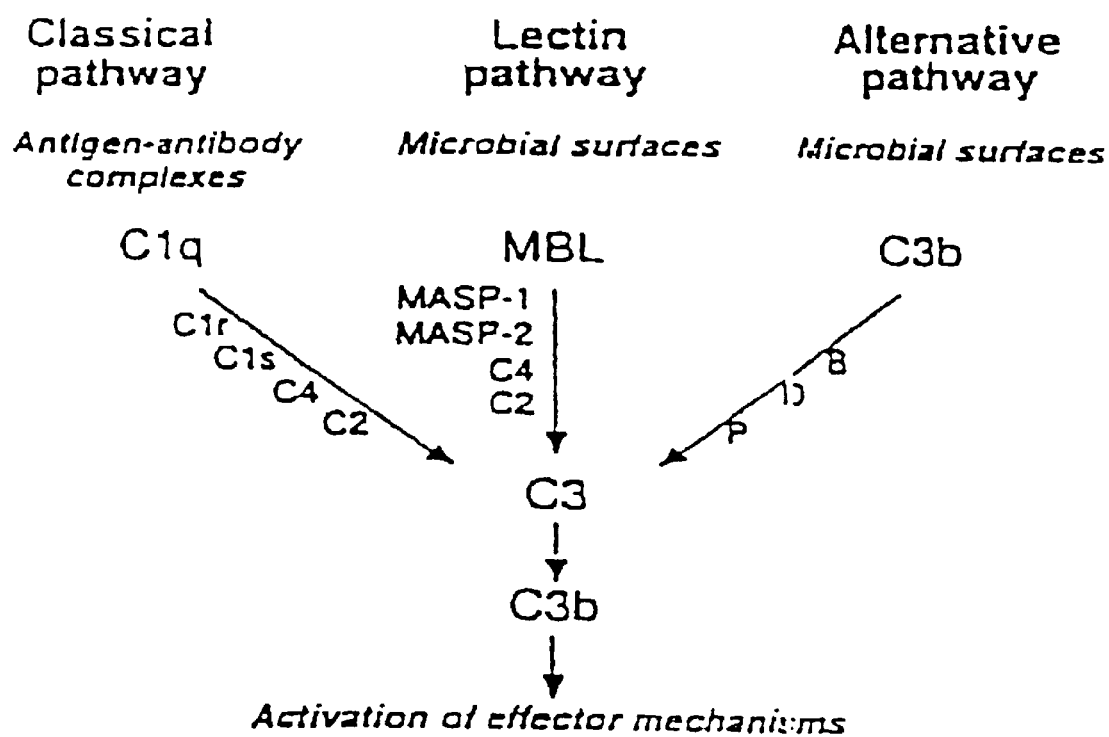
FIG. 5 illustrates the three pathways of complement activation.

Our results emphasize the similarity between complement activation through the MBLectin pathway of the innate immune system and the classical pathway of complement activation (FIG. 5). Activation via the classical pathway is associated with the specific immune response found only in vertebrates, while the MBLectin pathway and the alternative pathway rely on innate recognition of foreign organisms and are thus likely to predate the evolution of the specific immune system. All pathways converge on the activation of the central component C3 into C3b, which binds covalently to the microbial surface and mediates the effector functions of complement.

In both the classical and MBLectin pathways, the initiating molecular complexes are composed of an oligomeric ligand-binding component (MBL or C1q, respectively) which, on reacting with ligands, activates the two associated serine proteases (MASP-1 and MASP-2 or C1r and C1s, respectively).

REFERENCES

1) Law, S. K. A. & Reid, K. B. M. *Complement*, 2. ed. (Ed. Male, D.) 1–88 (In Focus, IRL Press, Oxford, 1996).

2) Ikeda, K., Sannoh, T., Kawasaki, N., Kawasaki, T. & Yamashina, I. Serum lectin with known structure activates complement through the classical pathway. *J. Biol. Chem.* 262, 7451–7454 (1987).

3) Kawasaki, T., Etoh, R. & Yamashina, I. Isolation and characterization of a mannan-binding protein from rabbit liver *Biochem. Biophys. Res. Commun.* 81, 1018–1024 (1978).

4) Matsushita, M. & Fujita, T. 4) Activation of the classical complement pathway by mannose-binding protein in association with a novel C1s-like serine protease *J. Exp. Med.* 176, 1497–1502 (1992).

5) Ji, Y-H. et al. Activation of the C4 and C2 components of complement by a proteinase in serum bactericidal factor, Ra reactive factor *J. Immumol.* 150, 571–578 (1993).

6) Turner, M. W. Mannose-binding lectin: the pluripotent molecule of the innate immune system. *Immnuol. Today*, 17, 532–540 (1996).

7) Kawasaki, N., Kawasaki, T. & Yamashina, I. A serum lectin (mannan-binding protein) has complement-dependent bactericidal activity. *J. Biochem.* 106, 483–489 (1989).

8) Kuhlman, M., Joiner, K. & Ezekowitz, R. A. B. The human mannose-binding protein functions as an opsonin. *J. Exp. Med.* 169, 1733–1745 (1989).

9) Sumiya, M. et al. Molecular basis of opsonic defect in immunodeficient children. *Lancet* 337, 1569–1570 (1991).

10) Lipscombe, R. J. et al. High frequencies in African and non-African populations of independent mutations in the mannose binding protein gene. *Hum. Mol. Genet.* 1, 709–715 (1992).

11) Madsen H. O. et al. A new frequent allele is the missing link in the structural polymorphism of the human mannan binding protein. *Immunogenetics* 40, 37–44 (1994).

12) Super, M., Thiel, S., Lu, J., Levinsky, R. J. & Turner, M. W. Association of low levels of mannan-binding protein with a common defect of opsonisation. *Lancet ii*, 1236–1239 (1989).

13) Garred, P., Madsen, H. O., Hofmann, B. & Svejgaard, A. Increased frequency of homozygosity of abnormal mannan binding-protein alleles in patients with suspected immunodeficiency. *Lancet* 346, 941–943 (1995).

14) Summerfield, J. A. et al. Mannose binding protein gene mutations associated with unusual and severe infections in adults. *Lancet* 345, 886–889 (1995).

15) Nielsen, S. L., Andersen, P. L., Koch, C., Jensenius, J. C. & Thiel, S. The level of the serum opsonin, mannan-binding protein in HIV-1 antibody-positive patients. *Clin. Exp. Immumol.* 100, 219–222 (1995).

16) Garred, P., Madsen, H. O., Balslev, U., Hofmann, B., Pedersen, C., Gerstoft, J. and Svejgaard, A. Susceptibility to HIV infection and progression of AIDS in relation to variant alleles of mannose-binding lectin. Lancet 349, 236–240 (1997).

17) Malhotra, R. Wormald, M. R., Rudd, P. M., Fischer, P. B., Dwek, R. A. and Sim, R. B. Glycosylation changes of IgG associated with rheumatoid arthritis can activate complement via the mannose-binding protein. Nature Med. 1, 237–243 (1995).

18) Kilpatrick, D. C., Bevan, B. H. and Liston, W. A. Association between mannan-binding protein deficiency and recurrent miscarriage. Mol. Hum. Reprod. 1, 2501–2505 (1995).

19) Davies, E. J., Snowden, N., Hillarby, M. C., Carthy, D. Grennan, D. M., Thomson, W. and Ollier, W. E. R. Mannose-binding protein gene polymorphism in systemic lupus erythematosus. Arthritis Rheum. 38, 110–114 (1995).

20) Jensenius, J. C. Mannan-binding lectin (MBL): From investigations on fish and chickens to substitution therapy in an infant with severe infections. Immunology, 86, Suppl. 1, 100, abstract (1995).

21) Garred, P., Madsen, H. O., Kurtzhals, J. A., et al. Diallelic polymorphism may explain variations of blood concentrations of mannan-binding protein in Eskimos but not in black Africans. Eur. J. Immunogenet. 19, 403–412 (1992).

22) Thiel, S., Jensen, T. V., Laursen, S. B., Willis, A. and Jensenius, J. C. Identification of a new mannan-binding protein associated serine protease (MASP-2). Immunology 86, Suppl. 1, 101 (1995).

23) Thiel, S., Jensen, T. V., Laursen, S. B., Willis, A., Reid, K. B. M., Hansen, S. and Jensenius, J. C. Identification of a new mannan-binding lectin associated serine protease (MASP-2). Mol. Immunol., 33, Suppl. 1, 91 (1996).

24) Jensen, T. V., Stover, C., Poulsen, K., Laursen, S. D., Eggleton, , P., Reid, K. B. M., Willis, A., Schwaeble, W., Lu, J., Holmskov, U., Jensenius, J. C. and Thiel, S. Cloning of cDNA encoding a human MASP-like protein (MASDP-2). Mol. Immunol., 33, Suppl. 1, 81 (1996).

25) Baatrup, G., Thiel, S., Isager, H., Svehag, S. E. & Jensenius, J. C. Demonstration in human plasma of a lectin activity analogous to that of bovine conglutinin. *Scand. J. Immumol.* 26, 355–361 (1987).

26) Jensenius, J. C., Andersen, I., Hau, J., Crone, M. & Koch, C. Eggs: conveniently packaged antibodies. Methods for purification of yolk IgG. *J. Immunol. Methods.* 46, 63–66 (1981).

27) Sato, T., Endo, Y., Matsushita, M. & Fujita, T. Molecular characterization of a novel serine protease involved in activation of the complement system by mannose-binding protein. *Int. Immumol.* 6, 665–669 (1994).

28) Endo, Y., Sato, T., Matsushita, M. & Fujita, T. Exon structure of the gene encoding the human mannose-binding protein-associated serine protease light chain: comparison with complement C1r and C1s genes. *Int. Immumol.* 9, 1355–1358 (1996).

29) Tan, S. M., Chung, M. C. M., Kon, O. L., Thiel, S. Lee, S. H. & Lu, J. Improvements on the purification of mannan-binding lectin and demonstration of its $Ca^{2+}$-independent association with a C1s-like serine protease. *Biochem. J.* 319, 329–332 (1996).

30) Barton, G. J. Protein multiple sequence alignment and flexible pattern matching. *Methods Enzymol.* 183, 403–428 (1990).

31) Takada, F., Takayama, Y., Hatsuse, H. & Kawakami, M. A new member of the C1s family of complement proteins found in a bactericidal factor, Ra-reactive factor, in human serum. *Biochem. Biophys. Res. Comm.* 196, 1003–1009 (1993).

32) Journat, A. & Tosi, M. Cloning and sequencing of full-length cDNA encoding the precursor of human complement component C1r. *Biochem. J.* 240, 783–787 (1986).

33) Lytus, S. P., Kurachi, K., Sakariassen, K. S. & Davie, E. W. Nucleotide sequence of cDNA coding for human complement C1r. *Biochemistry* 25, 4855–4863 (1986).

34) Mackinnon, C. M., Carter, P. E., Smyth, S. J., Dunbar, B. & Fothergill, J. E. Molecular cloning of cDNA for human complement component C1s. The complete amino acid sequence. *Eur. J. Biochem.* 169, 547–553 (1987).

35) Tosi, M., Duponchel, C., Meo, T. & Julier, C. Complete cDNA sequence of human complement C1s and close physical linkage of the homologous genes C1s and C1r. *Biochemistry* 26, 8516–8524 (1987).

What is claimed is:

1. A substantially pure polypeptide, which polypeptide comprises an amino acid sequence at least 95% identical to the sequence defined by position 16 to position 686 of SEQ ID NO:2,
   wherein said polypeptide has the following activities
   i) cleavage of C4 and activation of the complement in an in vitro assay for MBLectin complement pathway function; and
   ii) mannan-binding lectin (MBL) associating activity.

2. The polypeptide of claim 1 where said polypeptide binds a monoclonal antibody which binds mature MASP-2.

3. The polypeptide of claim 1 which comprises a contiguous 100 amino acid sequence which is completely identical to a sequence of 100 contiguous amino acids within the sequence from position 16 to position 686 of SEQ ID NO:2.

4. The polypeptide of claim 1 which comprises a sequence which, when aligned with SEQ ID NO:2, is identical to SEQ ID NO:2 at each position of SEQ ID NO:2 which is marked with an asterisk in FIG. 2 because it is a conserved residue position in MASP-2, MASP-1, C1r and C1s.

5. The polypeptide according to claim 1 in which differences between the amino acid sequence and the sequence defined by position 16 to position 686 of SEQ ID NO:2 are limited to substitutions selected from the group consisting of
   Gly/Ala,
   Val/Ile/Leu,
   Asp/Glu,
   Asn/Gln,
   Ser/Thr,
   Lys/Arg, and
   Phe/Tyr.

6. The polypeptide of claim 5 which comprises a sequence which, when aligned with SEQ ID NO:2, is identical to SEQ ID NO:2 at each position of SEQ ID NO:2 which is marked with an asterisk in FIG. 2 because it is a conserved residue position in MASP-2, MASP-1, C1r and C1s.

7. The polypeptide according to claim 1, in which the polypeptide comprises a sequence at least 98% identical to the sequence defined by position 16 to position 686 of SEQ ID NO:2.

8. The polypeptide of claim 7 which comprises a sequence which, when aligned with SEQ ID NO:2, is identical to SEQ ID NO:2 at each position of SEQ ID NO:2 which is marked with an asterisk in FIG. 2 because it is a conserved residue position in MASP-2, MASP-1, C1r and C1s.

9. The polypeptide according to claim 7 in which differences between the amino acid sequence and the sequence defined by position 16 to position 686 of SEQ ID NO:2 are limited to substitutions selected from the group consisting of
   Gly/Ala,
   Val/Ile/Leu,
   Asp/Glu,
   Asn/Gln,
   Ser/Thr,
   Lys/Arg, and
   Phe/Tyr.

10. The polypeptide of claim 9 which comprises a sequence which, when aligned with SEQ ID NO:2, is identical to SEQ ID NO:2 at each position of SEQ ID NO:2 which is marked with an asterisk in FIG. 2 because it is a conserved residue position in MASP-2, MASP-1, C1r and C1s.

11. The polypeptide according to claim 1, in which the polypeptide comprises a sequence at least 99% identical to the sequence defined by position 16 to position 686 of SEQ ID NO:2.

12. The polypeptide of claim 11 which comprises a sequence which, when aligned with SEQ ID NO:2, is identical to SEQ ID NO:2 at each position of SEQ ID NO:2 which is marked with an asterisk in FIG. 2 because it is a conserved residue position in MASP-2, MASP-1, C1r and C1s.

13. The polypeptide according to claim 11 in which differences between the amino acid sequence and the sequence defined by position 16 to position 686 of SEQ ID NO:2 are limited to substitutions selected from the group consisting of
   Gly/Ala,
   Val/Ile/Leu,
   Asp/Glu,
   Asn/Gln,
   Ser/Thr,
   Lys/Arg, and
   Phe/Tyr.

14. The polypeptide of claim 13 which comprises a sequence which, when aligned with SEQ ID NO:2, is identical to SEQ ID NO:2 at each position of SEQ ID NO:2 which is marked with an asterisk in FIG. 2 because it is a conserved residue position in MASP-2, MASP-1, C1r and C1s.

15. A substantially pure polypeptide consisting of the sequence of SEQ ID NO:2, or of the sequence defined by position 16 to position 686 of SEQ ID NO:2.

16. A substantially pure polypeptide comprising the amino acid sequence of position 16 to position 686 of SEQ ID NO:2.

17. A substantially pure polypeptide comprising the sequence identified as SEQ ID NO:1.

18. The polypeptide according to claim 17 with a molecular mass of about 20 k.

19. The polypeptide of claim 17, consisting of the sequence of SEQ ID NO:1.

20. A pharmaceutical composition comprising the polypeptide of claim 1.

* * * * *